(12) United States Patent
Osman

(10) Patent No.: US 11,872,019 B2
(45) Date of Patent: Jan. 16, 2024

(54) MRI-DERIVED STRAIN-BASED MEASUREMENTS AND RELATED IMAGE DATA ACQUISITIONS, IMAGE DATA PROCESSING, PATIENT EVALUATIONS AND MONITORING METHODS AND SYSTEMS

(71) Applicant: Myocardial Solutions, Inc., Morrisville, NC (US)

(72) Inventor: Nael F. Osman, Cary, NC (US)

(73) Assignee: Myocardial Solutions, Inc., Morrisville, NC (US)

( * ) Notice: Subject to any disclaimer, the term of this patent is extended or adjusted under 35 U.S.C. 154(b) by 434 days.

(21) Appl. No.: 16/880,110

(22) Filed: May 21, 2020

(65) Prior Publication Data

US 2020/0383584 A1 Dec. 10, 2020

Related U.S. Application Data

(60) Provisional application No. 62/857,314, filed on Jun. 5, 2019.

(51) Int. Cl.
*A61B 5/02* (2006.01)
*G01R 33/483* (2006.01)
(Continued)

(52) U.S. Cl.
CPC .......... *A61B 5/02028* (2013.01); *A61B 5/055* (2013.01); *A61B 5/7275* (2013.01);
(Continued)

(58) Field of Classification Search
CPC ... A61B 5/02028; A61B 5/055; A61B 5/7275; A61B 6/503; A61B 5/743;
(Continued)

(56) References Cited

U.S. PATENT DOCUMENTS 6,453,187 B1 9/2002 Prince et al.
6,597,935 B2 7/2003 Prince et al.
(Continued)

FOREIGN PATENT DOCUMENTS

JP 2013541385 A 11/2013
WO 2012055498 A1 5/2012
(Continued)

OTHER PUBLICATIONS

Cerqueira, M. D., et al., (2002) Standardized myocardial segmentation and nomenclature for tomographic imaging of the heart. A statement for healthcare professionals from the Cardiac Imaging Committee of the Council on Clinical Cardiology of the American Heart Association. Circulation, 105(4), 539-542 (Year: 2002).*
(Continued)

*Primary Examiner* — Hien N Nguyen
(74) *Attorney, Agent, or Firm* — Myers Bigel, P.A.

(57) ABSTRACT

Methods for providing MRI-derived strain measurements are described. Some methods include calculating a first set of strain measurements for each of a plurality of different segments of a heart over an entire single cardiac cycle from obtained MRI image data. Then, for each segment of the plurality of different segments, electronically identifying a peak train value and associated time point of the cardiac cycle in the first set of strain measurements; and electronically adjusting the first set of strain measurements at each time point of the cardiac cycle using the identified peak strain value as a reference peak strain value to thereby provide strain measurements that are adjusted relative to a defined time during the cardiac cycle irrespective of when signal acquisition of the obtained MRI image data was initiated during the cardiac cycle. Risk scores, contouring review, contraction pattern on a 3-D cardiac model are also disclosed.

19 Claims, 26 Drawing Sheets
(18 of 26 Drawing Sheet(s) Filed in Color)

(51) Int. Cl.
*A61B 5/00* (2006.01)
*G01R 33/563* (2006.01)
*A61B 5/055* (2006.01)
*G01R 33/56* (2006.01)

(52) U.S. Cl.
CPC ....... *G01R 33/4835* (2013.01); *G01R 33/563* (2013.01); *G01R 33/5608* (2013.01)

(58) Field of Classification Search
CPC ............ A61B 2576/023; A61B 5/1107; A61B 5/0044; G01R 33/4835; G01R 33/5608; G01R 33/563; G16H 15/00; G16H 20/00; G16H 30/20; G16H 30/40; G16H 50/50; G16H 50/30
See application file for complete search history.

(56) References Cited

U.S. PATENT DOCUMENTS

| | | | |
|---|---|---|---|
| 6,892,089 | B1 | 5/2005 | Prince et al. |
| 7,495,438 | B2 | 2/2009 | Prince et al. |
| 7,741,845 | B2 | 6/2010 | Osman |
| 7,800,366 | B1 | 9/2010 | Prince et al. |
| 8,380,281 | B2 | 2/2013 | Osman et al. |
| 8,380,286 | B2 | 2/2013 | Osman et al. |
| 9,024,971 | B2 | 5/2015 | Friedman et al. |
| 9,176,211 | B2 | 11/2015 | Cupps et al. |
| 10,524,687 | B2 | 1/2020 | Osman |
| 2004/0066958 | A1 | 4/2004 | Chen et al. |
| 2004/0153128 | A1 | 8/2004 | Suresh et al. |
| 2007/0014452 | A1 | 1/2007 | Suresh et al. |
| 2007/0016000 | A1 | 1/2007 | Prince et al. |
| 2007/0258631 | A1 | 11/2007 | Friedman et al. |
| 2008/0077032 | A1 | 3/2008 | Holmes et al. |
| 2008/0081997 | A1 | 4/2008 | Kakihara |
| 2009/0281415 | A1 | 11/2009 | Pasque et al. |
| 2010/0123714 | A1 | 5/2010 | Langeland et al. |
| 2010/0215238 | A1 | 8/2010 | Lu et al. |
| 2010/0280355 | A1 | 11/2010 | Grimm et al. |
| 2012/0121152 | A1 | 5/2012 | Lu et al. |
| 2013/0274592 | A1 | 10/2013 | Shin et al. |
| 2014/0121496 | A1 | 5/2014 | Bi et al. |
| 2014/0257083 | A1 | 9/2014 | McVeigh et al. |
| 2014/0347388 | A1 | 11/2014 | Friedman et al. |
| 2015/0077112 | A1 | 3/2015 | Otazo et al. |
| 2015/0133802 | A1 | 5/2015 | Nabutovsky et al. |
| 2015/0289769 | A1 | 10/2015 | Venkatesh et al. |
| 2015/0317448 | A1 | 11/2015 | Razavi et al. |
| 2016/0000392 | A1 | 1/2016 | Wong Po Foo et al. |
| 2016/0098833 | A1 | 4/2016 | Tsadok et al. |
| 2017/0065242 | A1 | 3/2017 | Chirvasa et al. |
| 2017/0332981 | A1 | 11/2017 | Witschey et al. |
| 2017/0337343 | A1 | 11/2017 | Kakadiaris et al. |
| 2018/0116725 | A1 | 5/2018 | Ashikaga et al. |
| 2019/0117073 | A1 | 4/2019 | Jolly et al. |
| 2019/0125309 | A1* | 5/2019 | Ramm .................. A61B 5/352 |

FOREIGN PATENT DOCUMENTS

| | | | |
|---|---|---|---|
| WO | 2014071126 A1 | 5/2014 | |
| WO | WO-2014071126 A1 * | 5/2014 | ........... A61B 5/0044 |

OTHER PUBLICATIONS

Abd-Elmoniem, K. Z., et al. (2008). Direct three-dimensional myocardial strain tensor quantification and tracking using zHARP. Medical image analysis, 12(6), 778-786 (Year: 2008).*

Gavara, J., et al. (2018). Prognostic Value of Strain by Tissue Tracking Cardiac Magnetic Resonance After ST-Segment Elevation Myocardial Infarction. JACC. Cardiovascular imaging, 11(10), 1448-1457 (Year: 2018).*

Pan et al. "Real-Time Imaging of Regional Myocardial Function Using Fast-SENC" Magnetic Resonance in Medicine, 55(2):386-395 (2006).

Cai et al. "Self-gated free-breathing cine DENSE imaging by adaptively reducing residual T1-echo energy" International Society for Magnetic Resonance in Medicine (ISMRM 2018), No. 0365 (5 pages) (Jun. 21, 2018).

Gavara et al. "Prognostic Value of Strain by Tissue Tracking Cardiac Magnetic Resonance After ST-Segment Elevation Myocardial Infarction" JACC: Cardiovascular Imaging, 11(10):1448-1457 (Dec. 2017).

Hung et al. "Longitudinal and Circumferential Strain Rate, Left Ventricular Remodeling, and Prognosis After Myocardial Infarction" Journal of the American College of Cardiology, 56(22):1812-1822 (Nov. 2010).

International Search Report and the Written Opinion of the International Searching Authority corresponding to International Patent Application No. PCT/US2020/034630 (23 pages) (dated Jan. 12, 2021).

Wang et al. "Self-gated Propeller-encoded cine cardiac imaging" The International Journal of Cardiac Imaging, 28(6):1477-1485 (Nov. 2011).

Korosoglou et al. "Fast Strain-Encoded Cardiac Magnetic Resonance for Diagnostic Classification and Risk Stratification of Heart Failure Patients" JACC: Cardiovascular Imaging, 14(6):1177-1188 (2021).

Pathan et al. "Normal Ranges of Left Atrial Strain by Speckle-Tracking Echocardiography: A Systematic Review and Meta-Analysis" Journal of the American Society of Echocardiography, 30(1):59-70 (2017).

Buckberg et al. "What is the heart? Anatomy, function, pathophysiology, and misconceptions" Journal of Cardiovascular Development and Disease, 5(33):1-29 (2018).

Cerqueira et al. "Standardized Myocardial Segmentation and Nomenclature for Tomographic Imaging of the Heart" Circulation, 105:539-542 (2002).

Choi et al. "Prognostic value of myocardial circumferential strain for incident heart failure and cardiovascular events in asymptomatic individuals: the Multi-Ethnic Study of Atherosclerosis" European Heart Journal, 34:2354-2361 (2013).

El Harouni, Ahmed "Enhancing Strain-Encoded (SENC) MRI for Breast and Cardiac Imaging" Dissertation submitted to Johns Hopkins University (178 pages) (Jan. 2011).

Kitkungvan et al. "Detection of LA and LAA Thrombus by CMR in Patients Referred for Pulmonary Vein Isolation" JACC: Cardiovascular Imaging, 9(7):809-818 (2016).

Neizel et al. "Strain-Encoded MRI for Evaluation of Left Ventricular Function and Transmurality in Acute Myocardial Infarction" Circulation: Cardiovascular Imaging, 2(2):116-122 (2009).

Sampath et al. "A combined harmonic phase and strain-encoded pulse sequence for measuring three-dimensional strain" Magnetic Resonance Imaging, 27(1):55-61 (2009).

Yousef et al. "The Effect of Noise on the Accuracy of Strain Measurement When Using Strain Encoded (SENC) MRI" Proceedings of the International Society of Magnetic Resonance in Medicine, 14:1658 (2006).

* cited by examiner

STRAIN TEST RESULTS 

PATIENT: 014_2b_110418     ACCESSION #:
ID:          ANONYMIZED    SCAN DATE:
GENDER:                    ORDERING PHYSICIAN:
DOB:                       SCANNING TECHNOLOGIST
AGE:         NA            EXAM TYPE:              MRZPM HERZMORPHOLOGIE
HEIGHT       183.0cm (6'0.0")  INDICATION:
WEIGHT:      67.0kg (147.7 lbs) STUDY QUALITY:
BSA:         1.87 m2

LV SEGMENTS (37/37 SEGMENTS ANALYZED)        14
NUMBER OF DYSFUNCTIONAL SEGMENTS (>-10%)      4
NUMBER OF ABNORMAL SEGMENTS (>-17%)          21

MYOHEALTH RISK SCORE
(%NORMAL SEGMENTS ≤-17%)
RS 43%    43%
100% 80% 60% 40% 20% 0%

SEGMENTAL MYOSTRAIN MEASUREMENTS

LONGITUDINAL STRAIN

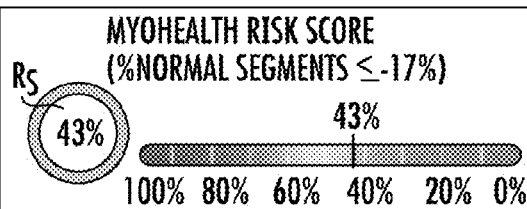

| | BASAL | | MID | | APICAL | |
|---|---|---|---|---|---|---|
| LV | ANTERIOR | -11.6% | ANTERIOR | -12.6% | ANTERIOR | -19.5% |
| | ANTEROSEPTAL | -11.8% | ANTEROSEPTAL | -15.8% | SEPTAL | -27% |
| | INFEROSEPTAL | -19.4% | INFEROSEPTAL | -19.8% | INFERIOR | -22.6% |
| | INFERIOR | -19.4% | INFERIOR | -17.6% | LATERAL | -19% |
| | INFEROLATERAL | -19.2% | INFEROLATERAL | -18.9% | | |
| | ANTEROLATERAL | -19.8% | ANTEROLATERAL | -16.2% | | |

-30%   -17%   -10%   0%   +10%

| | | | | |
|---|---|---|---|---|
| RV | ANTERIOR | -16.4% | ANTERIOR | -13.1% |
| | LATERAL | -19.9% | LATERAL | -21.6% |
| | INFERIOR | -22.7% | INFERIOR | -15.9% |

CIRCUMFERENTIAL STRAIN

| | 3CH | | 4CH | | 2CH | |
|---|---|---|---|---|---|---|
| | BASAL INFEROLATERAL | -7.9% | BASAL INFEROSEPTUM | -11.5% | BASAL INFERIOR | -12.5% |
| | MID INFEROLATERAL | -13.1% | MID INFEROSEPTUM | -17.7% | MID INFERIOR | -17.7% |
| | APICAL LATERAL | -7.2% | APICAL SEPTUM | -14.7% | APICAL INFERIOR | -21.6% |
| LV | APICAL CAP | -15.8% | APICAL CAP | -11.6% | APICAL CAP | -10.6% |
| | APICAL ANTERIOR | -13.3% | APICAL LATERAL | -10.6% | APICAL ANTERIOR | -12.5% |
| | MID ANTEROSEPTUM | -12.6% | MID ANTEROLATERAL | -18.4% | MID ANTERIOR | -19.6% |
| | BASAL ANTEROSEPTUM | -7% | BASAL ANTEROLATERAL | -15.5% | BASAL ANTERIOR | -9.8% |

-30%   -17%   -10%   0%   +10%

| | | | | |
|---|---|---|---|---|
| RV | BASAL ANTERIOR | -11.2% | BASAL LATERAL | -14.6% |
| | MID ANTERIOR | -15.9% | MID LATERAL | -11.5% |
| | | | APICAL LATERAL | -15.1% |

© 2020 MYCARDIAL SOLUTIONS, INC.

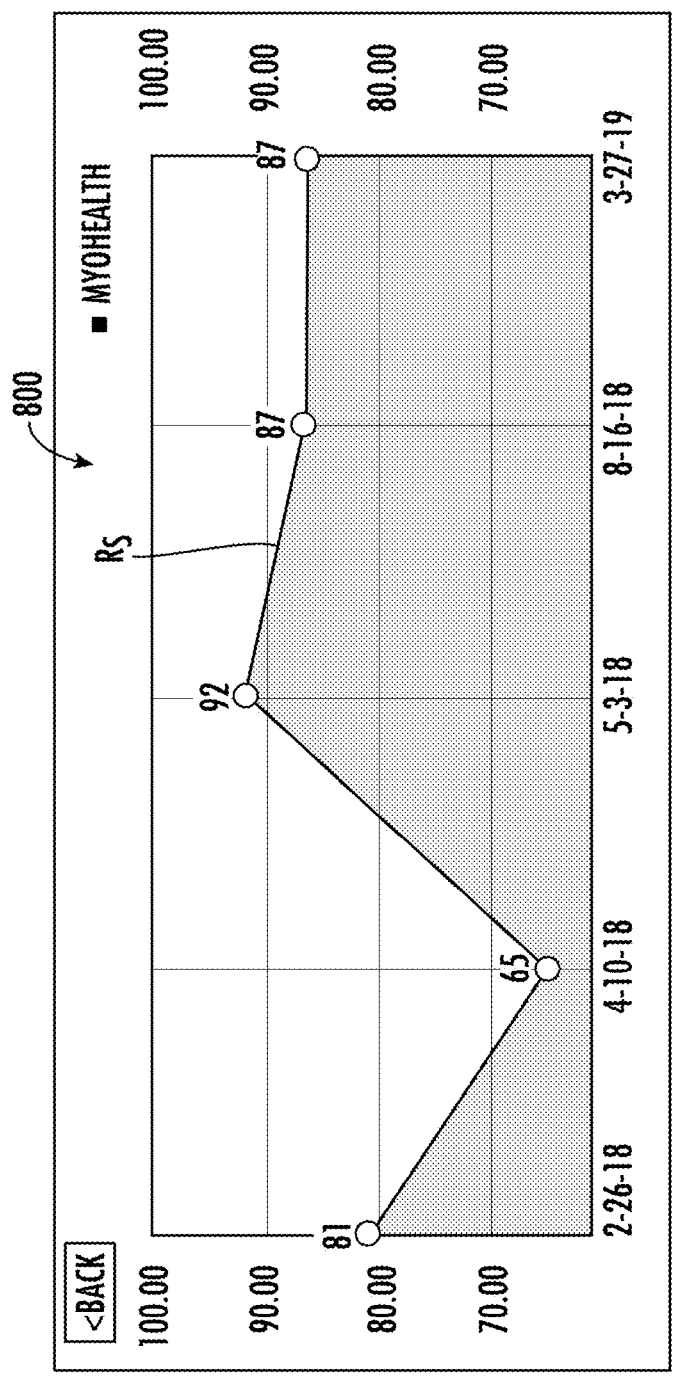

MRI-DERIVED STRAIN-BASED MEASUREMENTS AND RELATED IMAGE DATA ACQUISITIONS, IMAGE DATA PROCESSING, PATIENT EVALUATIONS AND MONITORING METHODS AND SYSTEMS

RELATED APPLICATIONS

This application claims the benefit of and priority to U.S. Provisional Application Ser. No. 62/857,314, filed Jun. 5, 2019, the contents of which are hereby incorporated by reference as if recited in full herein.

COPYRIGHT NOTICE

A portion of the disclosure of this patent document contains material which is subject to copyright protection. The copyright owner, Myocardial Solutions, Inc., has no objection to the reproduction by anyone of the patent document or the patent disclosure, as it appears in the Patent and Trademark Office patent file or records, but otherwise reserves all copyright rights whatsoever.

FIELD OF THE INVENTION

The present invention involves the field of Magnetic Resonance Imaging (MRI).

BACKGROUND

Improvements in medical imaging technologies, such as MRI, CT and ultrasound, have made it possible to image internal anatomical features in ways that show both structure and motion. Better diagnosis of certain medical conditions, such as heart disease, generally requires imagery that may be acquired quickly, and that provides information pertaining to both anatomical structure as well as function. Accordingly, there is an ongoing need for quantitative imaging of various tissue regions, such as the heart or other organs, which reduces the subjectivity and dependence on the experience of the reading physician.

Magnetic Resonance Imaging (MRI) has become a leading means of imaging for noninvasive diagnostics. By operating in regions of the electromagnetic spectrum that are benign to tissue, MRI imagery may be acquired repeatedly without danger to the patient. As used herein, the term "imagery" may refer to a single image or multiple images.

Non-MRI medical imaging technologies are generally not well suited for observer-independent imaging. These technologies, such as ultrasound, may involve invasive devices or cutaneous probes that may apply pressure to the patient's body in the vicinity of the tissue being imaged. As such, these imaging technologies may interfere with the function of certain organs by applying pressure, causing tissue deformations that may interfere with the motion and function of the tissue being imaged.

Conventional Mill procedures can be lengthy (at least 20 minutes) and involve the placement of patients inside the bore of the magnet for at least this duration of time. This has a number of disadvantages. The placement of a patient inside a closed bore magnet, which provides the best quality for imaging the heart, is extremely inconvenient for the patient and is very sensitive to any motion of the patient. In addition, lengthy breath-holds, where air is expelled before holding the breath, are required and images from multiple heartbeats are combined into a single traditional MRI cine. Compliance to the restriction of remaining still for extensive periods of time, particularly combined with lengthy breath-holds, can be extremely difficult for patients to maintain; as a result, acquired images of the heart frequently suffer from lower image quality. Also, extensive time inside the magnet is problematic for patients with different degrees of claustrophobia, which can cause additional motion that interferes with the imaging quality and can cause premature interruption or termination of the imaging, rendering the diagnostic information less than clinically satisfactory, if not worthless.

SUMMARY OF EMBODIMENTS OF THE INVENTION

Embodiments of the present invention are directed to systems, circuits and methods for measuring segmental contractility of muscle such as wall muscle of the heart, noninvasively, optionally also measuring regional and/or global function.

Embodiments of the invention are directed at rapid, quantitative cardiac evaluations, associated systems and methods, and cardiac risk scores comprising strain-based imaging techniques employing Strain ENCoded imaging (SENC), which is an MRI technique for imaging regional deformation of tissue, such as heart or other target muscle.

Embodiments of the present invention use multiple strain sequences along multiple acquisition planes that allow global and/or regional assessment of circumferential and longitudinal strain that correlate to myocardial contraction and function.

Embodiments of the invention are directed to risk scoring systems based on MRI Strain ENCoded (SENC) imaging that can generate risk scores to assess and/or quantify patient predisposition for developing heart failure and/or to assess a current status of the heart (from normal to one of several defined different stages of heart failure).

Embodiments of the invention can evaluate cardiotoxicity of pharmacological agents as well as efficacy of cardioprotective medications. In addition, embodiments of the invention can evaluate treatments of patients with (structural) heart disease to determine timing and efficacy of such interventions.

Embodiments of the present invention integrate regional circumferential and longitudinal strain parameters into at least one risk score associated with a patient's functional cardiac status. The at least one risk score can identify a patient's risk of developing or having heart failure. The at least one risk score can identify a degree of current heart failure. The at least one risk score may be used to track progression of diseases, cardiotoxicity of pharmaceutical drugs such as chemotherapy agents, impact of cardioprotective medications in patients exhibiting regional or global dysfunction, and ischemia for coronary artery disease or microvascular obstruction, for example. The at least one risk score may be used in clinical trials to evaluate a drug's impact on cardiac function, for example.

Embodiments of the invention can integrate regional circumferential and longitudinal strain parameters in a 3-dimensional heart model. This 3-dimensional heart model can be color-coded to visually portray circumferential and longitudinal contraction to thereby provide visualization of changes in contraction pattern across patients with similar clinical conditions and/or applications and/or between testing time points for individual patients.

Embodiments of the invention provide reports, outputs of displays of cardiac models of respective patients of serial HIPAA compliant exams to show changes in regional and global strain parameters including one or more cardiac risk score. In particular embodiments, reports can include and/or provide a QR code that includes testing information that can be scanned with a camera of a computer device, optionally a mobile device, using a mobile application and/or computer software application to automatically obtain and allow a user to display progressive changes in patient function as well as a customized three-dimensional model of the heart illustrating the patient's cardiac function using strain measurements of contractility.

Embodiments of the invention provide methods, systems and circuits that employ a rapid strain encoding (SENC) pulse sequence to acquire, in a single heartbeat, a sequence of images of heart muscle functionality during the cardiac cycle and within a slice (plane) of the heart. This series of SENC raw images can be combined together to obtain an anatomical sequence and a strain sequence of the heart muscle in that slice. The SENC raw sequence with high tuning shows the tissue of the heart at end-systole as bright in contrast to lung tissue and blood that show darker, typically much darker, than the bright tissue. This contrast allows for fast segmentation of (i.e., isolating in images) the heart muscle to separate from other tissues of the body. The anatomical sequence shows the tissue of the heart as bright as the rest of the tissue of the body while suppressing the signal of the blood inside the heart cavities (known as black blood imaging). The strain sequence shows measurements of the contraction and relaxation of the heart muscle during the cardiac cycle; providing measurements of the contractility of the heart muscle. Further discussion of exemplary SENC pulse sequences and protocols can be found in one or more of U.S. Pat. No. 6,597,935: Method for harmonic phase magnetic resonance imaging; U.S. Pat. No. 7,741,845: Imaging tissue deformation using strain encoded MRI; and U.S. Pat. No. 7,495,438: Three dimensional magnetic resonance motion estimation on a single image plane. The contents of these documents are hereby incorporated by reference as if recited in full herein.

Embodiments of the invention are directed to methods of adjusting MRI-derived strain measurements. The methods include calculating a first set of strain measurements for each of a plurality of different segments of a heart over an entire single cardiac cycle from obtained MRI image data. Then, for each segment of the plurality of different segments, electronically identifying a peak strain value and associated time point of the cardiac cycle in the first set of strain measurements; and electronically adjusting the first set of strain measurements at each time point of the cardiac cycle using the identified peak strain value as a reference peak strain value to thereby provide strain measurements that are adjusted relative to a defined time during the cardiac cycle irrespective of when signal acquisition of the obtained Mill image data was initiated during the cardiac cycle.

The obtained MRI image data can be obtained asynchronously to begin acquisition at a random point in the cardiac cycle without triggering or gating to an ECG signal.

The peak strain value can be defined as "strain-p", and the adjustment can be carried out for each of the first set of strain measurements for all corresponding strain values for each of the plurality of segments at each time using the mathematical relationship: strain_N=(strain_O−strain_p)/(100+strain_p) in %, where strain_N is a new (adjusted) strain value and strain_O is a first strain value from the first set of strain measurements.

Embodiments of the invention include an MRI workstation configured with or in communication with at least one processor and/or server configured to carry out the methods hereinabove.

Other aspects of the invention are directed to methods of providing MRI-derived strain measurements that include: obtaining a plurality of parallel slices of a common (the same) single image plane; and for each slice of the parallel slices, calculating a strain value for each of a plurality of segments; and for each segment of the plurality of segments, combining one or more strain measurements from at least two corresponding segments of different slices of the plurality of slices to thereby generate a composite strain value for each segment.

The combining can be carried out to average two or more strain values from at least two corresponding segments of different slices.

The average can be a weighted average whereby one strain value is given a greater multiplier or weight than another for a respective segment.

The single imaging plane can be a two-chamber long-axis view of the heart. The plurality of slices can be three. The number of segments can be seven.

Embodiments of the invention include an MRI workstation configured with or in communication with at least one processor and/or server configured to carry out the method hereinabove.

Embodiments of the invention are directed to methods of providing MRI-derived strain measurements. The methods include: obtaining a plurality of parallel slices of a common (the same) single image plane; and for each slice of the parallel slices, calculating a strain value for each of a plurality of segments; and for each segment of the plurality of segments, selecting a peak strain value from one of the calculated strain values of the plurality of slices as a resultant strain value for that segment.

The single imaging plane can be a two-chamber long-axis view of the heart. The plurality of slices can be three, and the number of segments can be seven.

Embodiments of the invention include an MRI workstation configured with or in communication with at least one processor and/or server configured to carry out the method hereinabove.

Embodiments of the invention are directed to methods of identifying potential contouring and/or segmentation errors in MRI images. The methods include electronically reviewing strain measurements of defined segments of long and short axis views of a heart of a patient defined in MRI images based on a first contouring of myocardium tissue between inner and outer boundaries; then for each view, electronically determining whether an average strain measurement for all segments is greater than a defined cut off value and, if so, identifying a respective view as needing a review of the first contouring. The methods also include electronically determining whether a number of segments of the defined segments have a strain measurement above −17% exceeds a defined threshold and, if so, identifying a respective view as needing a review of the first contouring; and electronically determining whether any segment of the defined segments has strain that is greater than −10 exits, and, if so, identifying a respective view as needing a review of the first contouring.

The methods can also include electronically calculating global measurements of the heart of the patient including ejection fraction (EF) and left ventricle mass and volume parameters based, at least in part on the MRI images and the first contouring; then electronically determining whether the ejection fraction (EF) is less than a defined value, and, if so identifying at least one long axis view as needing a review of the first contouring; and electronically determining whether any of the left ventricle mass and volume parameters are greater or less than respective defined values and, if so, identifying at least one long axis view as needing a review of the first contouring.

Embodiments of the invention include an MRI workstation or module in communication with or configured with at least one processor and/or server configured to carry out the method hereinabove.

Yet other embodiments are directed to methods of providing cardiac strain information of a patient. The methods include generating at least one three-dimensional heart model visually showing MRI derived strain measurements of cardiac tissue using visual vectors and/or color-coded strain values correlated to position in or on the at least one three-dimensional model.

The at least one three-dimensional model can be provided as a cine of three-dimensional models of a cardiac cycle with the strain measurements. The visual vectors and/or color-coded strain values can change in image frames of the cine and can be correlated to times in a cardiac cycle.

The MRI-derived strain measurements can include longitudinal and circumferential strain measurements from short and long axis slices of the heart.

The at least one three-dimensional heart model can be a standardized heart model with different defined ranges of strain values shown in different colors as the color-coded strain values.

The different colors can include first, second and third colors for different defined percentages of strain measurements. The first, second and third colors can reflect different percentages of strain extending across and through volumes of the at least one three-dimensional heart model.

The visual vectors can be provided in different sizes, including first, second and third sizes for different defined percentages of strain measurements, with the first and second sizes having lengths and/or widths that are different from the third size.

The strain measurements can include peak strain.

The strain measurements can include systolic or diastolic strain rate.

The at least one three-dimensional model can provide a visual illustration of a duration of peak strain as one or more of the strain measurements.

The strain measurements can include midmyocardial strain including one or more of: peak strain, strain rate, duration of peak strain, or time to peak strain, or other strain metric.

The strain measurements can include endocardial or epicardial strain.

The strain measurements can be visually shown on the at least one three dimensional model to visually illustrate a contraction profile.

Embodiments of the invention include an MRI workstation or module in communication with or configured with at least one processor and/or server configured to carry out the methods hereinabove.

Yet other embodiments are directed to methods of monitoring and/or assessing cardiac health. The methods include: obtaining a plurality of strain measurements derived from MRI images of a heart of a patient; and programmatically calculating a risk score using the plurality of strain measurements. The risk score is provided in a numerical range with a first end of the range associated with a healthy (normal) heart and a second end of the range corresponding to heart failure thereby providing a measure of current status of cardiac health.

The plurality of strain measurements can include circumferential and longitudinal strain measurements.

The risk score can define a linear relationship of progressive left ventricular dysfunction over the range.

A mid-range value of the risk score can define an at-risk and/or pre-heart failure status.

The risk score can be provided as a percentile score. The numerical range can be 0%-100%.

The strain measurements can include strain measurements for longitudinal left ventricular segments and circumferential left ventricular segments.

The longitudinal left ventricular segments can include sixteen segments: 6 basal-, 6 mid-, and 4-apical short axis, and the circumferential left ventricular segments can include twenty one segments: 7 two-chamber, 7 three-chamber, and 7 four-chamber long axis.

The risk score can be calculated using the mathematical relationship for at least one region of the heart, optionally a left ventricle region:

$$\text{Risk Score} = \frac{\left(\begin{array}{l}(\text{\# Longitudinal Segments} \leq -17\%) + \\ (\text{Circumferential Segments} \leq -17\%)\end{array}\right)}{\text{Total \# of Long. and Cir. Segments}} \times 100.$$

Embodiments of the invention include an MRI workstation or module in communication with or configured with at least one processor and/or server configured to carry out any of the methods hereinabove.

Further features, advantages and details of the present invention will be appreciated by those of ordinary skill in the art from a reading of the figures and the detailed description of the preferred embodiments that follow, such description being merely illustrative of the present invention.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF DRAWINGS

The patent or application file contains at least one drawing executed in color. Copies of this patent or patent application publication with color drawings will be provided by the Office upon request and payment of the necessary fee.

FIG. 14 is an example examination report that shows both the risk score and segmental (peak) midmyocardial strain values according to embodiments of the present invention.

FIGS. 16A-16C are example displays provided by functions of a mobile application that can scan the QR code in FIG. 15 and/or otherwise obtain data from the report in FIG. 14 and can display 3-D models and progression of cardiac risk scores according to embodiments of the present invention.

DETAILED DESCRIPTION

Figure 1:
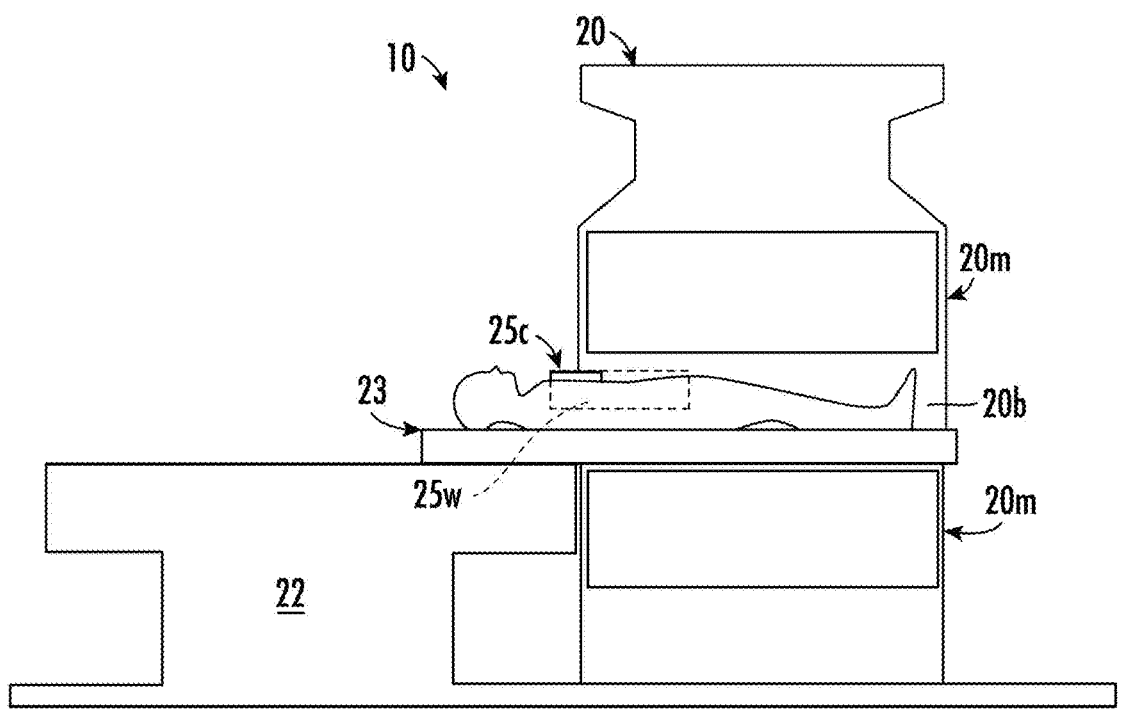
FIG. 1 is a schematic illustration of an example MRI scanner system according to embodiments of the present invention.

The present invention now will be described more fully hereinafter with reference to the accompanying drawings, in which illustrative embodiments of the invention are shown. Like numbers refer to like elements and different embodiments of like elements can be designated using a different number of superscript indicator apostrophes (e.g., 10, 10', 10", 10'"). The terms "Fig." and "FIG." may be used interchangeably with the word "Figure" as abbreviations thereof in the specification and drawings. In the figures, certain layers, components or features may be exaggerated for clarity, and broken lines illustrate optional features or operations unless specified otherwise.

In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below.

The term "about" refers to numbers in a range of +/−20% of the noted value.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

Embodiments of the invention are intended to improve the ability of MRI imaging to more quickly quantify and/or provide standardized reports that identify heart abnormalities and trends for physicians to direct patient management and/or treatment.

The term "circuit" refers to an entirely software embodiment or an embodiment combining software and hardware aspects, features and/or components (including, for example, a processor and software associated therewith embedded therein and/or executable by, for programmatically directing and/or performing certain described actions, operations or method steps).

The term "programmatically" means that the operation or step can be directed and/or carried out by a digital signal processor and/or computer program code. Similarly, the term "electronically" means that the step or operation can be carried out in an automated manner using electronic components rather than manually or using any mental steps.

The terms "MM scanner" and MR scanner" are used interchangeably to refer to a Magnetic Resonance Imaging system and includes the high-field magnet and the operating components, e.g., the RF amplifier, gradient amplifiers and processors that typically direct the pulse sequences and select the scan planes. Examples of current commercial scanners include: GE Healthcare: SIGNA 1.5T/3.0T; Philips Medical Systems: Achieva™ 1.5T/3.0T; Philips Intera™ 1.5T; Siemens: MAGNETOM Avanto®; MAGNETOM Espree®; MAGNETOM Symphony™; MAGNETOM Trio®; and MAGNETOM Verio®; United Imaging: uMR® 570; uMR® 780; uMR Omega®; uMR® 790; uPMR® 790 PET/MR. It is contemplated that both vertical and horizontal bore MM scanner systems may be used. In addition, MRI scanners combined with other functions such as radiotherapy, PET imaging, or other therapeutic or imaging technology may be utilized.

As is well known, the MR scanner can include a main operating/control system that is housed in one or more cabinets that reside in an MR control room while the MRI magnet resides in the MR scan suite. The control room and scan room can be referred to as an MR suite and the two rooms can be separated by an RF shield wall. The term "high-magnetic field" refers to field strengths above 0.5 T, typically above 1.0 T, and more typically between about 1.5 T and 10 T. Embodiments of the invention may be particularly suitable for 1.5 T and 3.0 T systems, or higher field systems such as future contemplated systems at 4.0 T, 5.0 T, 6.0 T, 7 T, 8 T, 9 T and the like. Embodiments of the invention may also be useful with lower field portable MRI scanner systems.

The methods and systems can also be applied to animal MRI data acquired from animal MRI scanners but may be particularly suitable for human patients.

The term "patient" refers to humans and animals. Embodiments of the invention may be particularly suitable for human patients.

The term "automatically" means that the operation can be substantially, and typically entirely, carried out without manual input, and is typically programmatically directed and/or carried out. The term "electronically" with respect to connections includes both wireless and wired connections between components.

The term "clinician" means physician, radiologist, cardiologist, physicist, technician, nurse, physician assistant, or other medical personnel desiring to review medical data of a patient.

The term "workstation" refers to a display and/or computer associated with an MR scanner. The workstation and/or computer or circuit with at least one processor can communicate the MR scanner, can be partially or totally onboard the MR scanner and can be remote from the MR scanner, for access by a clinician.

Embodiments of the present invention may take the form of an entirely software embodiment or an embodiment combining software and hardware, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices. Some circuits, modules or routines may be written in assembly language or even microcode to enhance performance and/or memory usage. It will be further appreciated that the functionality of any or all of the program modules may also be implemented using discrete hardware components, one or more application specific integrated circuits (ASICs), or a programmed digital signal processor or microcontroller. Embodiments of the present invention are not limited to a particular programming language.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on the user's computer, partly on the user's computer, as a stand-alone software package, partly on the user's computer and partly on another computer, local and/or remote or entirely on the other local or remote computer. In the latter scenario, the other local or remote computer may be connected to the user's computer through a local area network (LAN) or a wide area network (WAN), or the connection may be made to an external computer (for example, through the Internet using an Internet Service Provider).

Embodiments of the invention may be carried out using a cloud computing service (or an aggregation of multiple cloud resources), generally referred to as the "Cloud". Cloud storage may include a model of networked computer data storage where data is stored on multiple virtual servers, rather than being hosted on one or more dedicated servers. Firewalls and suitable security protocols can be followed to exchange and/or analyze patient data.

Strain imaging techniques that have improved upon traditional MRI techniques include Strain ENCoded imaging (SENC), which is an MRI technique for imaging regional deformation of tissue, such as the heart muscle. Prior, related art developments in MRI are not capable of providing high quality imagery of tissue that includes a quantitative measure of tissue deformation. SENC is able to measure movement of the heart muscle itself without relying on calculation of changes between the epicardium and endocardium to estimate regional wall motion. Directly measuring myocardial wall motion with SENC eliminates errors derived from manual estimation that hinder prior MRI or Non-MRI techniques of evaluating heart functionality.

Referring to FIG. 1, the MRI system 10 uses an MRI scanner 20 with a magnetic field magnet 20m (1.5 T, 3 T or even greater or lower magnetic field strength). The term "scanner" is used interchangeably with the capitalized version "Scanner" herein. The patient can be positioned on top of a translatable MRI tabletop 23 held by a table 22. The tabletop 23 can move and slide into and out of the MRI magnet bore 20b. This motion can be controlled from inside the MRI magnet room or from the console outside the magnet room (in the control room of an MRI suite, for example). Specialized or conventional RF coils 25 for imaging the thorax or the heart can be used. The RF coil 25 can be a body coil. The RF coil 25 can be a chest coil. The RF coil 25 can be configured as a chest and thoracic coil or a full body coil 25w that may be utilized to evaluate cardiac function during the same scan session for non-cardiac scans. For example, cardiac scans with SENC may be performed while concurrently or serially scanning lungs for cancerous tumors or other abnormalities while a patient remains in a bore of the magnet of the MRI scanner 20. Embodiments of the invention can be useful for other applications such as orthopedic, neurological, or other non-cardiac application that can utilize any suitable RF coil 25 and that may benefit from cardiac clearance and/or monitoring (with SENC) during the same scan session. It is also noted that two separate RF coils may also be used instead one RF coil 25. Although the patient can be in any suitable position for imaging, a representative position for heart patients is to lie on their backs and enter the MRI feet first. It is also noted that vertical bore systems may also be used.

Figure 2A:
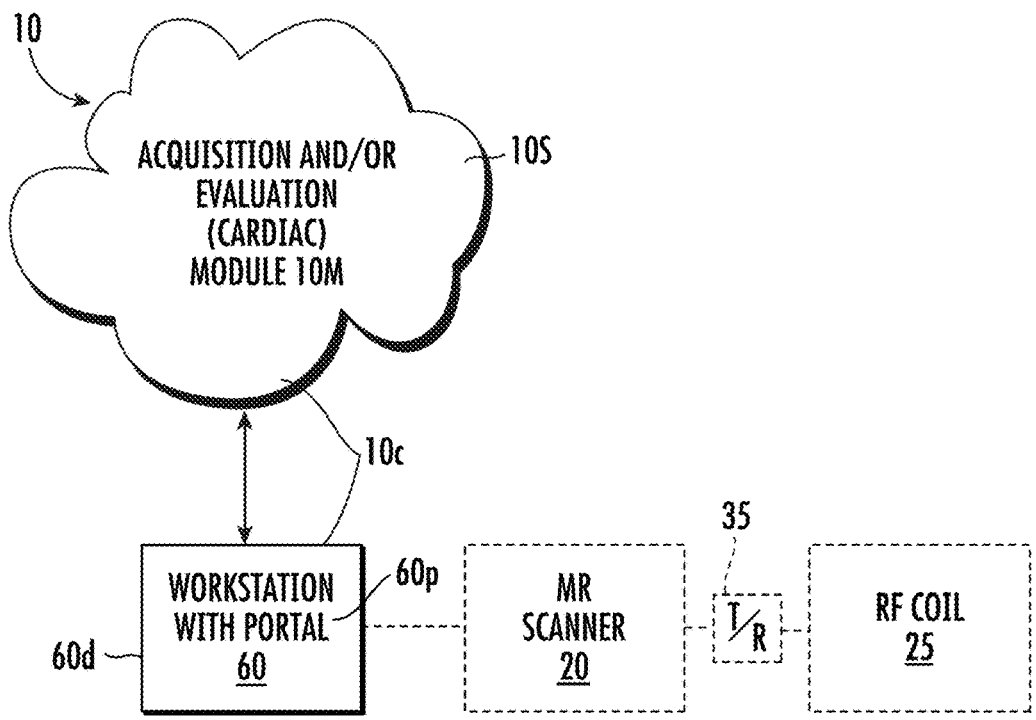
FIGS. 2A-2C are schematic illustrations of different configurations of example MRI systems according to embodiments of the present invention.
Figure 2B:
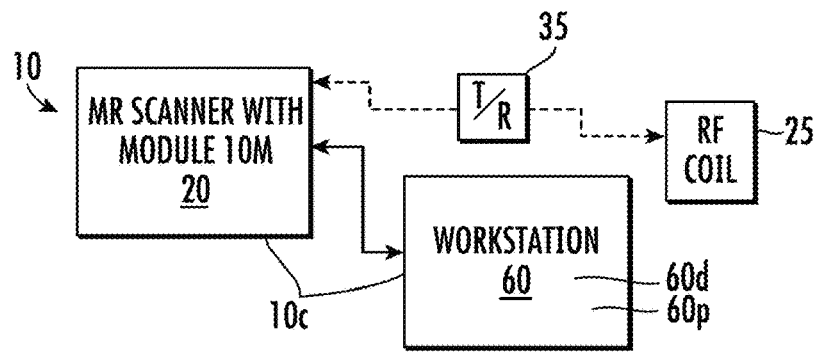
Figure 2C:
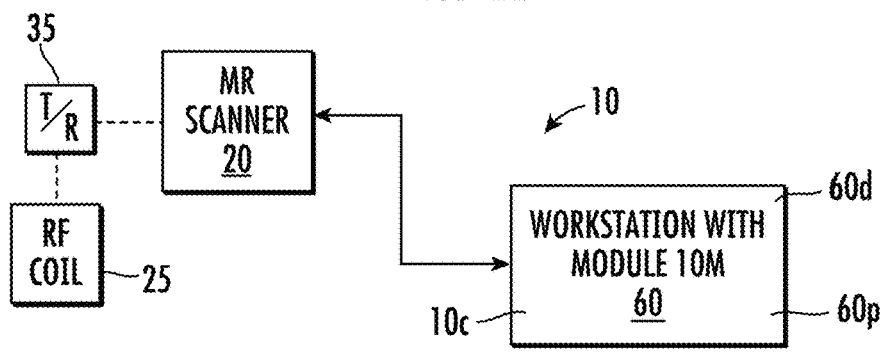

FIGS. 2A-2C are schematic illustrations of different configurations of the MRI imaging system 10 according to embodiments of the present invention. The MRI imaging system incorporates an MR Scanner 20 with a high-magnetic field magnet 20m having a bore 20b, and includes the SENC pulse sequence and a workstation 60. The workstation 60 communicates with an image acquisition, image processing and/or image evaluation cardiac (SENC) module 10M and the module 10M can contain the software to generate the SENC pulse sequence and create strain sequences and optionally compile the outcomes into standardized reports and/or heart models of global and regional values of circumferential and longitudinal strain that correlate to strain measurements (optionally regarding myocardial contraction and function). The workstation 60 can include a display 60d. The system 10 can include a circuit 10c with at least one processor for image processing the obtained MIII images and/or can comprise one or both of an SENC pulse sequence and/or other strain sequence modalities and calculations that is/are onboard or remote from the workstation and comprises the module 10M. The system 10 can include a T/R switch 35 that can communicate with the RF coil 25.

FIG. 2A illustrates that the system 10 can include at least one workstation 60 that has a portal for accessing the circuit 10c and/or cardiac module 10M. The circuit 10c may include at least one processor configured to provide the SENC pulse sequences, analyze the raw SENC images and/or calculate the strain measurements. The module 10M can be held on a remote server accessible via a LAN, WAN or Internet. The workstation 60 can communicate with the MR Scanner 20 and an RF coil 25. The MR Scanner 20 typically directs the operation of the pulse sequence and image acquisition using the RF coil 25 and at least on transmit/receive switch 35 as is well known to those of skill in the art. The RF coil 25 can be any suitable coil, such as, for example, a thoracic or chest coil or whole-body coil as discussed above. The workstation 60 can include a display 60d with a GUI (graphic user input) and the access portal 60p. The workstation 60 can access the module 10M via a relatively broadband high-speed connection using, for example, a LAN or may be remote and/or may have lesser bandwidth and/or speed, and for example, may access the data sets via a WAN and/or the Internet. Firewalls may be provided as appropriate for security.

FIG. 2B illustrates that the module 10M can be partially or totally included in the MR Scanner 20 (i.e., a control console or computer) which can communicate with a workstation 60. The module 10M can be integrated into the control cabinet of the MR Scanner with image processing circuitry. The workstation 60 can be in the magnet room and/or the control room of an MRI suite or may be remote from the MRI suite.

FIG. 2C illustrates that the module 10M can be integrated into one or more local or remote workstations 60 that communicates with the MR Scanner 20. Although not shown, parts of the module 10M can be held on both the Scanner 20 and one or more workstations 60, which can be remote or local.

Some, or all, of the cardiac module 10M can be held on at least one server 10S that can communicate with one or more MR scanners 20. The at least one server 10S can be provided using cloud computing which includes the provision of computational resources on demand via a computer network. The resources can be embodied as various infrastructure services (e.g., compute, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. Firewalls and suitable security protocols can be followed to exchange and/or analyze patient data.

Strain Encoded Imaging (SENC) is an MRI technique for imaging regional deformation of tissue, such as the heart muscle or other muscle or muscle groups. Embodiments of the invention can use a SENC pulse sequence, other tagging based, or non-tagging based pulse sequence to acquire a movie (a series of successive MRI images) of strain during a time period, such as, for example, a single heartbeat in a single view of a respective cut/slice of the heart using Mill. Multiple strain sequences are then acquired from predefined cuts (the word "cuts" is also referred to interchangeably herein as "slices" or "planes") of the heart to quantify global and regional values of circumferential and longitudinal strain that correlate to (myocardial if the heart) contraction and function. See, e.g., co-pending, co-assigned U.S. patent application Ser. No. 15/498,058 which issued in U.S. Pat. No. 10,524,687, the contents of which are hereby incorporated by reference as if recited in full herein.

Embodiments of the present invention are described further below.

Asynchronous Image Data Acquisition/ECG-Free SENC Scan

Cardiac MRI imaging, in general, requires the use of multiple heartbeats to reconstruct a full movie of the moving heart, thus triggering is typically considered essential to conventional MRI scans. An ECG signal can be used to trigger the SENC scan at certain points in the cardiac cycle (e.g., during a QRS complex at a time corresponding to end-diastole). One reason that necessitates the use of ECG signal in traditional MRI scans is to align the partial acquisitions of different portions of the heart at different phases of the cardiac cycle. Because SENC only requires a single heartbeat acquisition, it does not require ECG triggering for acquiring the images. However, SENC can utilize ECG triggering to time the acquisition to the cardiac cycle, when needed.

SENC acquisition using a single heartbeat pulse sequence can be performed asynchronously. In this scenario, the SENC strain will be measured correctly, but values will be referenced to a random point. If the scan is triggered at end-diastole, then all the strain values will be negative, indicating contraction/shortening of the myocardium. However, if the triggering is at end-systole, then all the strain values in the ventricles will be positive, indicating relaxation/lengthening of the myocardium. Any other point will relay mixed results by some negative and some positive. Embodiments of the invention can employ an asynchronous SENC image data acquisition. The asynchronous acquisition can compute/calculate strain values relative to a random trigger point during a cardiac cycle to provide a first set of strain curves, but then adjust the first strain curves using a defined reference point of a cardiac (QRS) cycle, such as end-diastole, in order to obtain a temporally standardized strain curve, hence, peak strain, strain rates, and other key strain parameters.

The asynchronous SENC acquisition does not use ECG signal triggering or gating, which provides a number of benefits. First, cardiac imaging with strain can be applied in many cases where obtaining proper ECG signal is not possible or is problematic which can increase clinical utility and/or facilitate ease of use. For example, in patients with Atrial Fibrillation (AF) or other types of arrhythmias, eliminating ECG triggering or gating can allow SENC image acquisition when traditional ECG signals may have low amplitude or poor morphology of the ECG across the cardiac cycle. Eliminating the requirement to have a good quality ECG for triggering or gating to specific features of the ECG can allow SENC image acquisition irrespective of cardiac rhythm, patient body habitus (larger patients frequently have poor ECG signals), loss of signal quality due to slippage of ECG electrodes, or noise interference. Second, avoiding the need for ECG triggering or gating can simplify the exam and can reduce the time for patient preparation by eliminating the time required to place the ECG leads on the patient and ensure proper signal quality without interference from other electronic equipment. Third, avoiding the need for ECG triggering or gating can avoid or reduce the cost associated with ECG equipment and/or electrodes thereby decreasing exam costs. Finally, eliminating the need for ECG triggering or gating can allow or facilitate SENC cardiac scanning with non-cardiac MRI exams during a single scan session by avoiding the use of electrodes that may create artifacts when imaging the thoracic cavity adjacent to the locations of the ECG electrodes, for example.

Figure 3A:
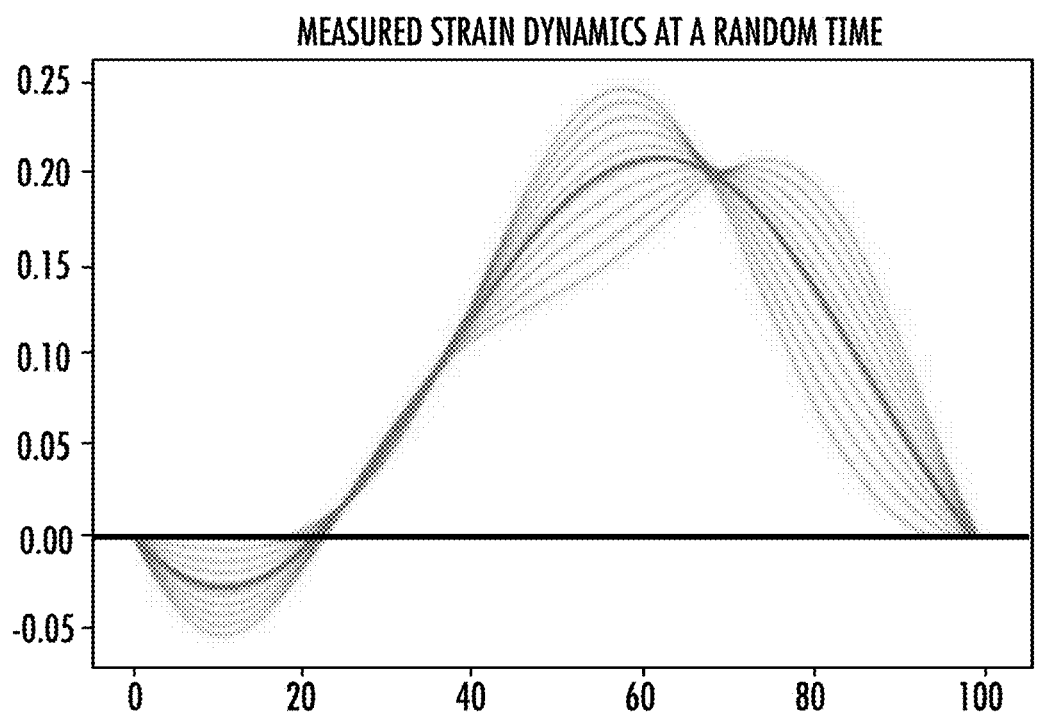
FIGS. 3A-3B are example strain curves taken at different time points along the cardiac cycle that can be corrected to allow ECG-free analysis to measure intramyocardial strain according to embodiments of the invention.

Image acquisition without ECG triggering will result in obtaining strain in reference to an arbitrary or random point in the cardiac cycle. In the example measured strain curves shown in FIG. 3A, the image acquisition likely started close to end-systole, when the ventricles are almost fully contracting with minimal volume of the chambers. As a result, the resulting strain values reflect the relaxation of the ventricles as they are filled with blood, hence showing positive values of strain at time points close to time=20 (x-axis in this example shows percent of cardiac cycle) and thereafter.

Figure 3B:
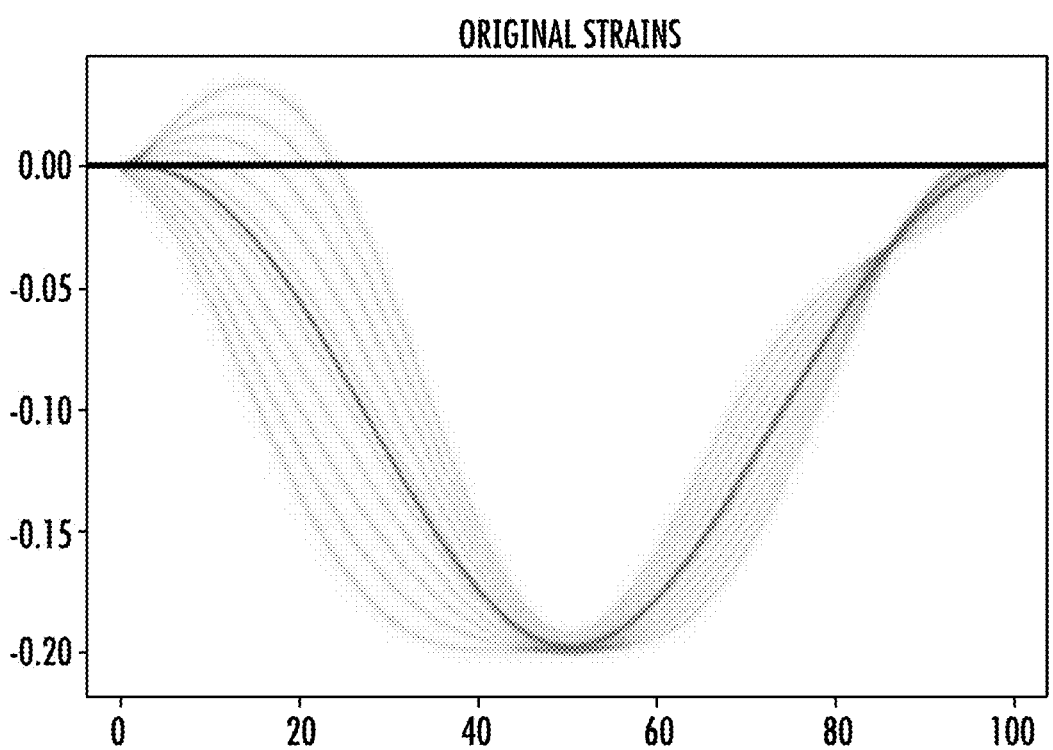

In another representative example as shown in FIG. 3B, the strain curves are referenced to end-diastole. In this case, most of the strain values are in the negative region demonstrating the overall contraction of the heart muscle to reduce the volume with the ventricular chamber, thus ejecting the blood to circulate in body and lung arteries.

Figure 3C:
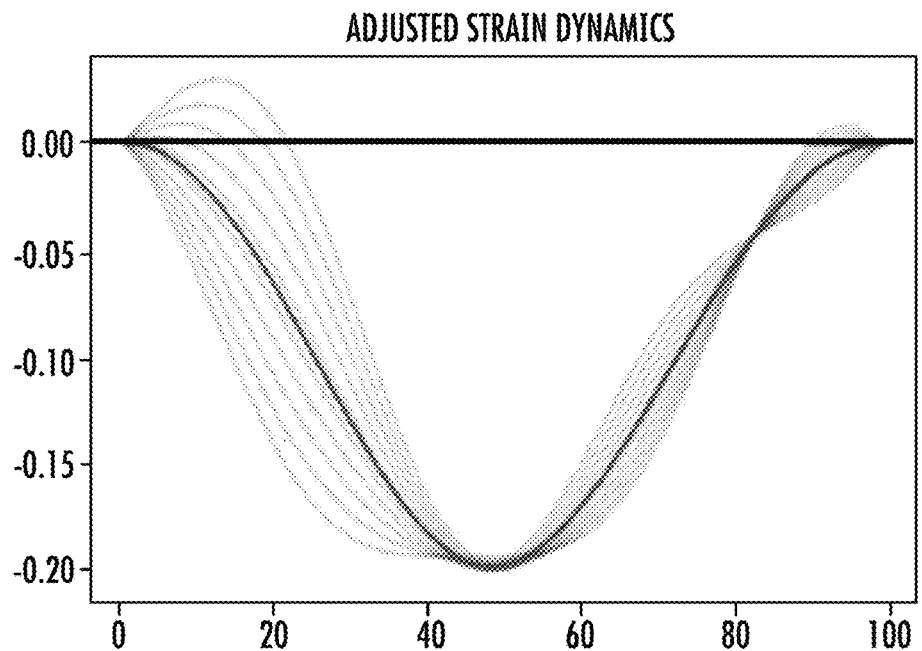
FIG. 3C is an adjusted strain curve of the strain curve of FIG. 3A.
Figure 3D:
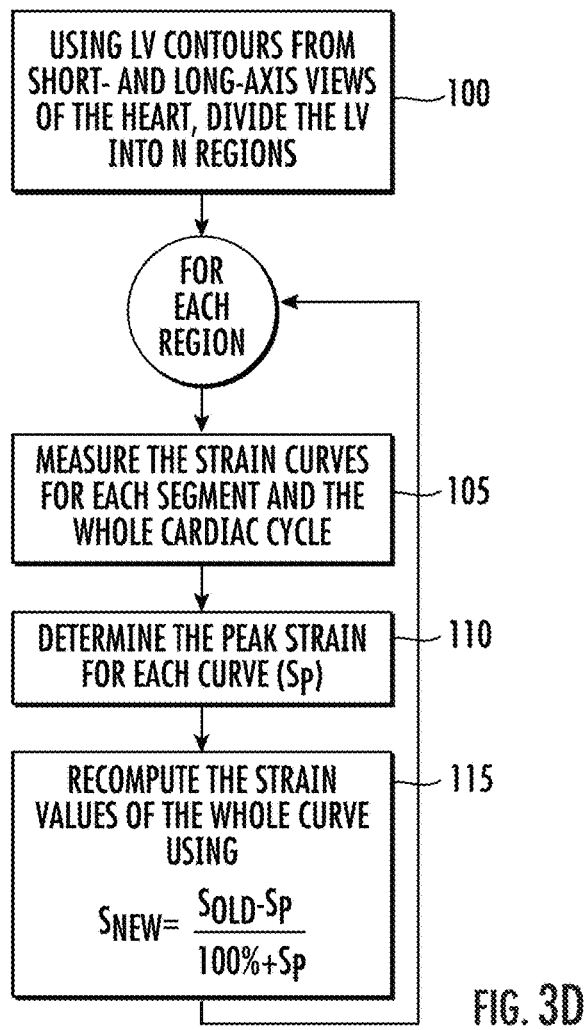
FIG. 3D is a flow chart of actions that can be carried out to provide the adjusted strain curves to allow ECG-free SENC exams according to embodiments of the invention.

Using the asynchronous acquisition method, the strain curves obtained starting at any time point during the cardiac cycle can be adjusted to reflect the selection of a specific or defined reference point in the cardiac cycle. In this example, the selected reference point is when the chambers of the heart are at/of maximum average strain values. Therefore, the first set of strain curves are adjusted, as shown in FIG. 3C, into a standard form corresponding to when ECG triggering is used and done at end-diastole. Referring to FIG. 3D, example actions to adjust the first set of strain curves acquired starting at a random point in the cardiac cycle are shown.

The left ventricle ("LV") is virtually/electronically divided into a number "N" of defined regions or segments (block 100). LV contours from short and long axis views can be used to so divide the LV into the defined regions or segments. N is typically a number in a range of 3-30 for each image plane. In a representative example, long-axis (2-chamber, 3-chamber, and 4-chamber) image planes are each divided into 7 circumferential LV strain segments while basal- and mid-short axis image planes are divided into 6 longitudinal LV strain segments and the apical-short axis is divided into 4 LV segments; this provides a total of 37 segments for all image planes in the representative example. The right ventricle ("RV") may also be divided typically into 2-15 segments for each image plane. It should be noted that with enough computing power, a much larger number of segments may be utilized to increase spatial resolution when analyzing various results from the acquired image sequences.

For each region or segment, strain is measured for an entire (single) cardiac cycle (block 105). The time at which there is the highest strain value or "peak strain" will be considered to correspond to end-diastole of the cardiac cycle. A strain value at that time will be selected as the new reference strain of zero value. This peak strain value can be defined as "strain_p" or "$s_p$") (block 110).

All the strain values for all the regions or segments at each time are adjusted as follows:

$$\text{strain\_}N = (\text{strain\_}O - \text{strain\_}p)/(100 + \text{strain\_}p) \text{ in \%}. \quad \text{Equation (1)}$$

Where strain_N is the new strain value and strain_O is the old strain value (block 115).

Measuring Strain from Parallel Slices

It is possible to acquire multiple long-axis planes (or short axis planes or other atypical planes) parallel to each other for a certain view. FIG. 4E is a diagram showing an example of a plurality of parallel cuts or slices S1, S2, S3 of a heart H that produce three cuts of a single image plane of the left ventricle. Although shown as three, two or more than three cuts/slices can be used. The cuts/slices S1, S2, S3 are closely spaced apart, typically a distance of 0.25 mm-10 mm. Because SENC is a vector-based approach, each cut of the single image plane in a respective view can (typically will) produce different strain measurements, which can be used to produce more reliable and/or accurate measurements of strain for each segment in that view. The strain measurements can be circumferential strain measurements derived from parallel long axis slices of the heart. Alternatively, the same methodology may be applied to parallel short axis slices for longitudinal strain or atypical planes for alternative strain vectors. It should be noted that SENC can be used to measure multiple planes of not only the left ventricle, but also the right ventricle, the left atrium, the right atrium, the aorta, and other cardiac or non-cardiac muscle tissue.

Referring to FIGS. 4A-4D, the measurements from the different slices S1, S2, S3 of a respective view can be selected or combined to provide final measurements for that specific view. For example, the planes for the 2-chamber image plane are shown relative to short-axis views in FIG. 4A. The 2-chamber planes are parallel to each other but will produce different strain measurements. In each row of FIG. 4A, the specific long-axis plane that is selected (numbered box) is shown and its intersections with the corresponding different short-axis planes are shown in the left three images (basal, mid, and apical columns) in the row.

Figure 4A:
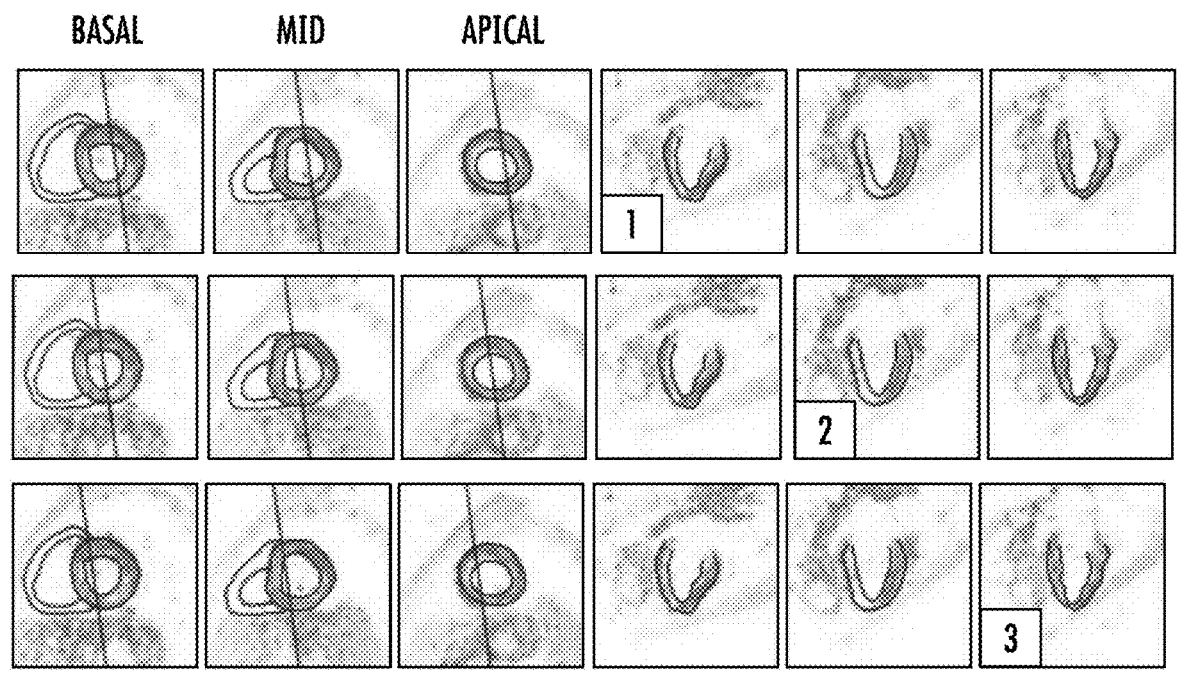
FIG. 4A are SENC short and long axis images taken from multiple parallel planes that can be used to improve and/or optimize calculated regional and global intramyocardial strain measurements according to embodiments of the invention.
Figure 4B:
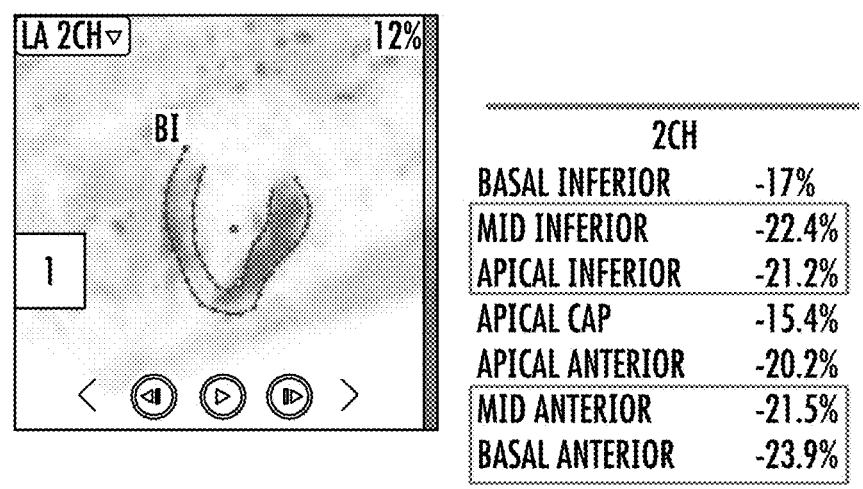
FIG. 4B is an enlarged long axis view of a two chamber image corresponding to labeled panel 1 of FIG. 4A with corresponding strain measurement data.
Figure 4C:
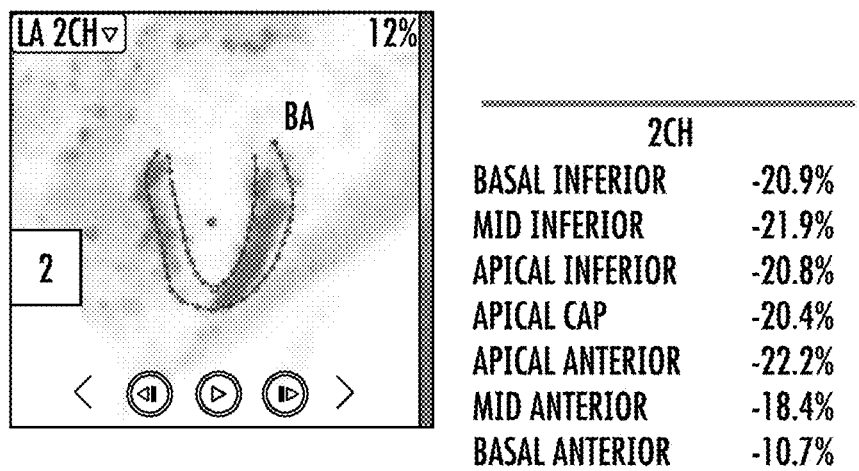
FIG. 4C is an enlarged long axis view of a two chamber image corresponding to labeled panel 2 of FIG. 4A with corresponding strain measurement data.
Figure 4D:
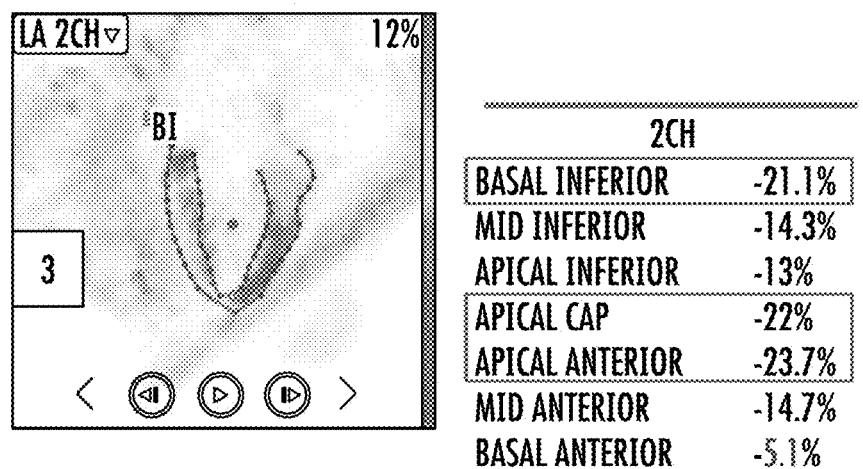
FIG. 4D is an enlarged long axis view of a two chamber image corresponding to labeled panel 3 of FIG. 4A with corresponding strain measurement data.
Figure 4E:
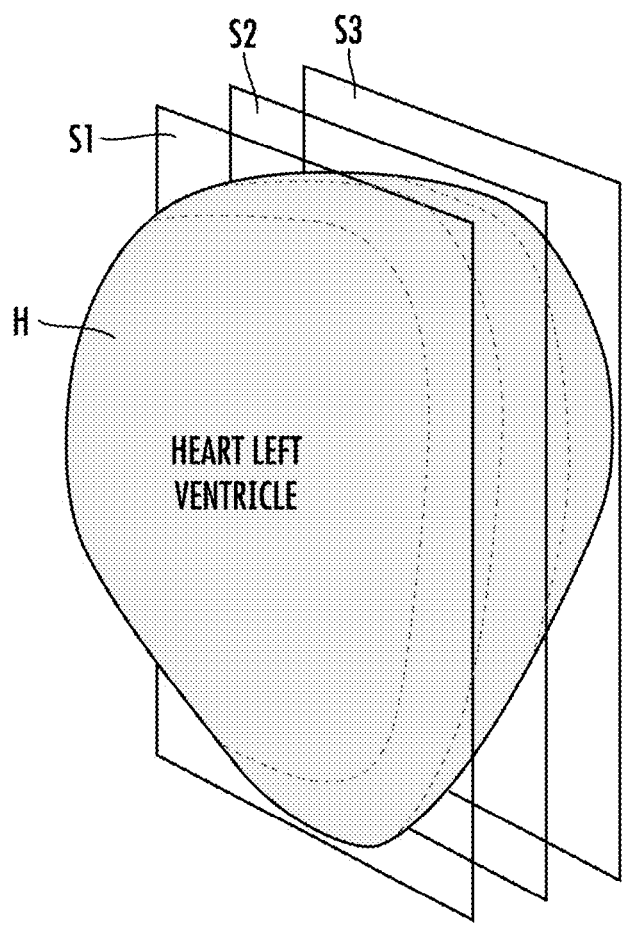
FIG. 4E is a schematic diagram showing three parallel planes producing three cuts/slices of a single view of the left ventricle which can be evaluated to provide the images of FIG. 4A and strain data shown in FIGS. 4B-4D according to embodiments of the present invention.

The (peak midmyocardial) strain measurements for each segment of the three 2-chamber planes 1, 2, 3 in FIG. 4A are shown in FIGS. 4B, 4C, and 4D. In the representative case, the 2-chamber plane (same as for the 3-chamber and 4-chamber planes) is sectioned into a plurality of regions or segments, such as 7 segments as shown, with the segments labeled basal inferior, mid inferior, apical inferior, apical cap, apical anterior, mid anterior and basal anterior. It should be noted that each long-axis plane (as well as short axis planes) can be segmented into any number of segments to achieve a clinically acceptable representation of cardiac function.

In this example, some peak strain measurements of a respective segment are found in FIGS. 4B and 4D but not in FIG. 4C. From the three slices in FIGS. 4B, 4C, and 4D, a composite set of peak (midmyocardial) strain measurements with respective segment measurements selected from one of the three slices 1, 2, 3 can be used to produce the final (7) strain measurements by selecting a peak (midmyocardial) strain value of each segment from one of the three slices, for example. Thus, in this example, the strain measurements for each segment is:

| | |
|---|---|
| basal inferior | −21.1% |
| mid inferior | −22.4% |

-continued

| | |
|---|---|
| apical inferior | −21.2% |
| apical cap | −22.0% |
| apical anterior | −23.7% |
| mid anterior | −21.5% |
| basal anterior | −23.9% |

Figure 4F:
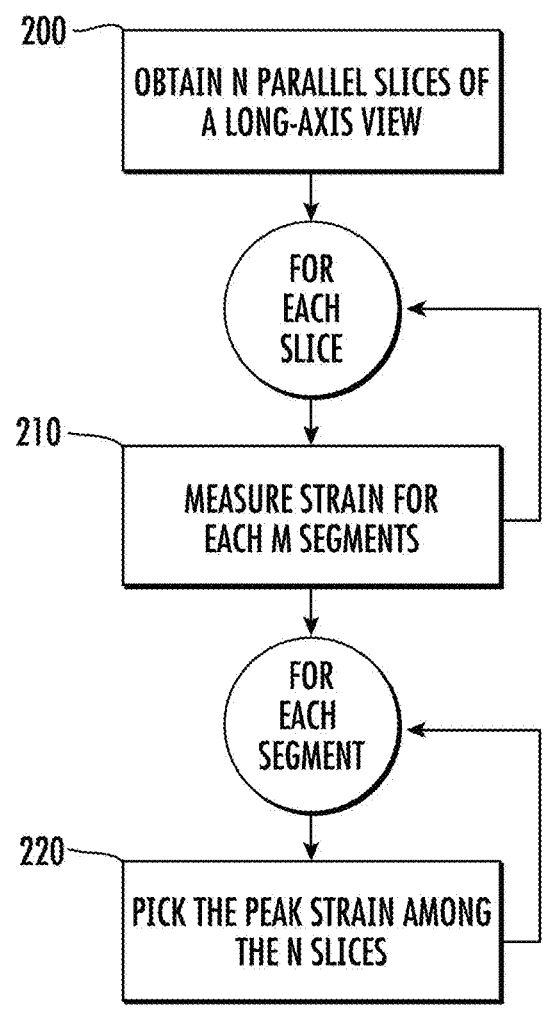
FIG. 4F is a flow chart of actions that can be carried out to provide strain metrics from parallel slices as shown in FIGS. 4A-4D, according to embodiments of the present invention.

FIG. 4F is a flow chart of example actions that can be used to select the strain measurements for a respective segment from different parallel slices using this peak strain technique.

A plurality "N" of parallel slices of a common (the same) single image plane (such as, but not limited to a two-chamber long-axis view) are obtained (block 200). For each slice, strain for each of a plurality of segments is calculated/measured (block 210). For each segment, a strain measurement that is a peak strain is selected from one corresponding segment among the N slices (block 220) to thereby generate a composite result of different peak strains for each respective segment irrespective of which of the N slices that peak measurement value is associated with.

This representative case of the 2-chamber long axis plane discussed by way of example with respect to FIGS. 4A-4E, applies to other image planes including the 3-chamber and 4-chamber long axis planes, all short axis planes, and any atypical plane. Alternative integration of multiple parallel slices of a single image plane (in the representative case, the 2-chamber long axis) may be utilized instead of taking the peak midmyocardial strain for each segment from a respective slice.

For example, an average of strain values of corresponding segments in the parallel slices may be utilized which may even be weighted based on the accuracy of the image plane calculated by evaluating how close the image plane is to ideal based on the locations of the plane relative to the short axis planes and/or other long-axis planes. A weighted average may give greater importance to those planes closest to the ideal short axis but ensure changes in fiber orientation due to clinical disease progression are incorporated when producing the integrated segmental strain report.

Figure 4G:
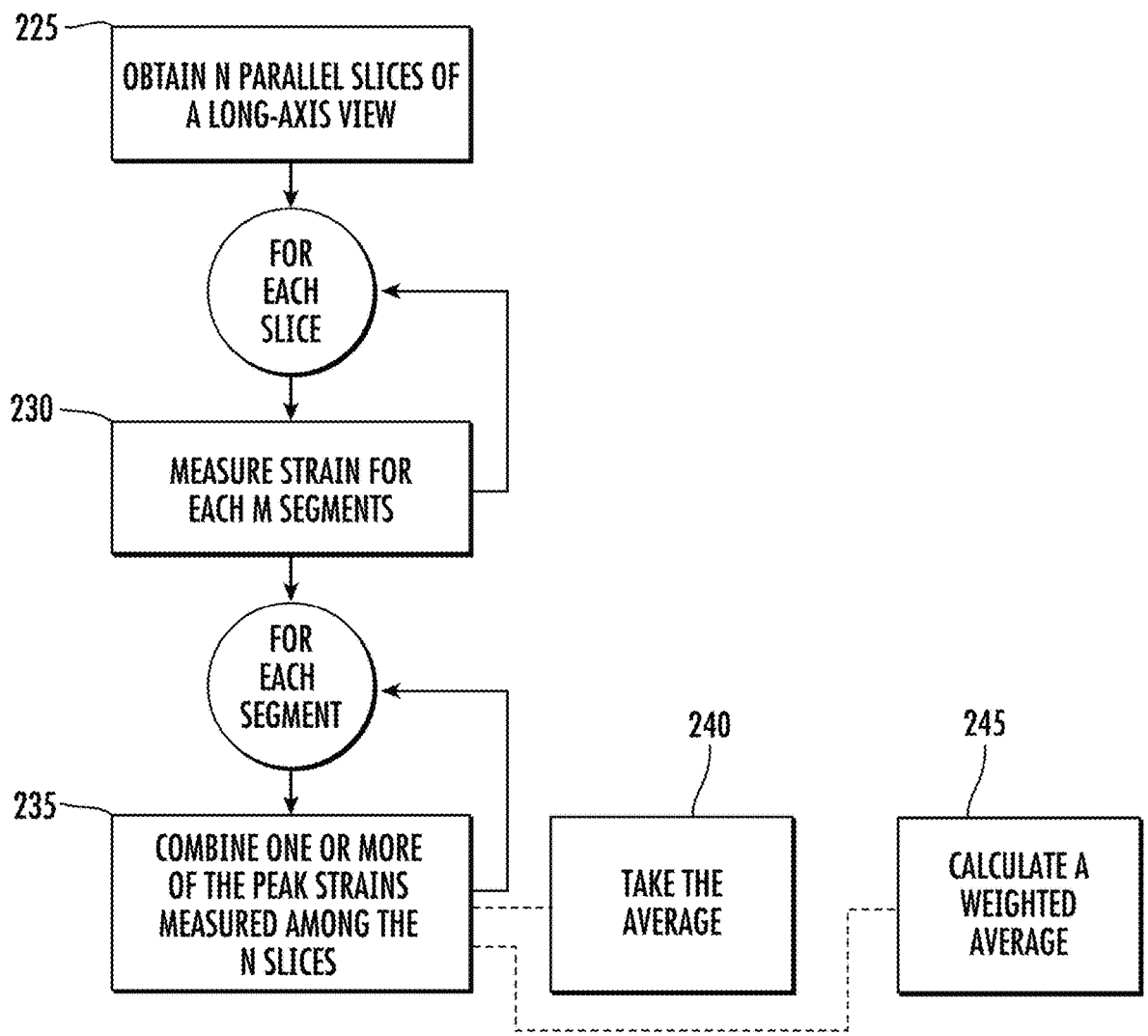
FIG. 4G is another flow chart of actions that can be carried out to provide strain metrics for respective segments from parallel slices, according to embodiments of the present invention.

FIG. 4G is a flow chart of example actions that can be used to provide a combined strain measurement for a respective segment from different parallel slices. Thus, similar to FIG. 4F, a plurality "N" of parallel slices of a common (the same) single image plane (such as, but not limited to a two-chamber long-axis view) are obtained (block 225). For each slice, strain for each of a plurality of segments is calculated/measured (block 210). For each segment, strain measurements from at least two corresponding segments among the N slices are combined (block 235) to thereby generate a composite result of strain for each respective segment. Optionally, an average of two or more strain values of a respective segment in the single view can be used to define a respective strain value of a segment in the single view block (240). Optionally, the average can be a weighted average whereby one strain measurement is given a greater multiplier or weight than another for a respective segment (block 245).

Again, it is noted that the representative example and alternative techniques discussed above for the 2-chamber long axis plane can be applied to any other long-axis, short axis, or atypical plane, including but not limited to a 3-chamber long axis, 4-chamber long axis, basal short axis, mid short axis, and apical short axis planes.

Efficient Auto Contouring

As used herein, the terminologies regarding contouring, segmentation and healthy myocardium or region thereof are described for clarity. Contouring refers to the curves that delineate the boundaries of the myocardium. There are two of them, an outer contour (epicardial) and an inner contour (endocardial). Segmentation refers to the region of the myocardium in-between the outer and inner contours. This region is divided into segments for the different regions of the heart. These segments may be divided perpendicular to the contours at prespecified or predefined points; for example, in the representative example, the long-axis planes are divided into 7 segments, the basal and mid short axis planes are divided into 6 segments, and the apical short axis plane is divided into 4 segments. The planes may be divided into equal segments or unequal segments to account for the morphology of the heart. These segments may additionally be segmented parallel to the contouring to include endocardial, midmyocardial, and epicardial layers.

Healthy myocardium, or a region of myocardium with normal contraction, refers to tissue whose strain value is less than or equal to −17%. Since strain is a metric of contraction, strain should have a negative value, and the more negative the stronger the contraction. So a healthy strain is less than or equal to −17% (e.g. −19%).

SENC images shows strain within the myocardium (see, U.S. patent application Ser. No. 15/498,058, incorporated by reference hereinabove). There is no need for any extra post processing in order to compute the strain throughout the cardiac cycle. However, segmentation of the ventricles can be important in order to generate a clinical report showing segmental strain values. Also, it can be important for computing traditional measurements, such as ejection fraction, masses and volumes.

Contouring can be done manually. For example, a user can draw contours at the inside and outside of the heart to differentiate the myocardium from the other parts of the image. This process is not typically tedious or time consuming, as only 6 views are required to be contoured with MyoStrain® MRI system evaluation tools to obtain strain measurements. The MyoStrain® MRI system is available from Myocardial Solutions Inc., Morrisville, NC, "myocardialsolutions.com".

Nevertheless, for other applications such as calculating the peak strain (e.g., maximum absolute strain) from various slices or displaying the strain curves over time may require more contours; therefore, replacing manual contouring with automatic or semi-automatic contouring can reduce the total analysis time and/or reduce the dependence on the expertise of the analyst, promoting more reliable test reports.

Note: 100% sensitivity, but not perfect specificity. That is, an image identified with healthy strain is typically guaranteed to be well segmented. However, an image with unhealthy strain(s), might be badly segmented but with the operator having the ability to edit the contours.

Embodiments of the present invention can use resultant strain measurements in each respective patient test or exam report to guide a contouring review process of that patient. Embodiments of the invention can configure the module 10M (FIGS. 2A-2C) to provide the contouring review.

Weak strain measurement(s) can be a result of a weak heart (a heart with reduced ability to properly contract), or badly planned by the technologist or badly contoured by the user of the software. However, normal strain results cannot be attributed to bad planning or mis-contouring. A completely normal strain is in no way a mistake.

Figure 5:
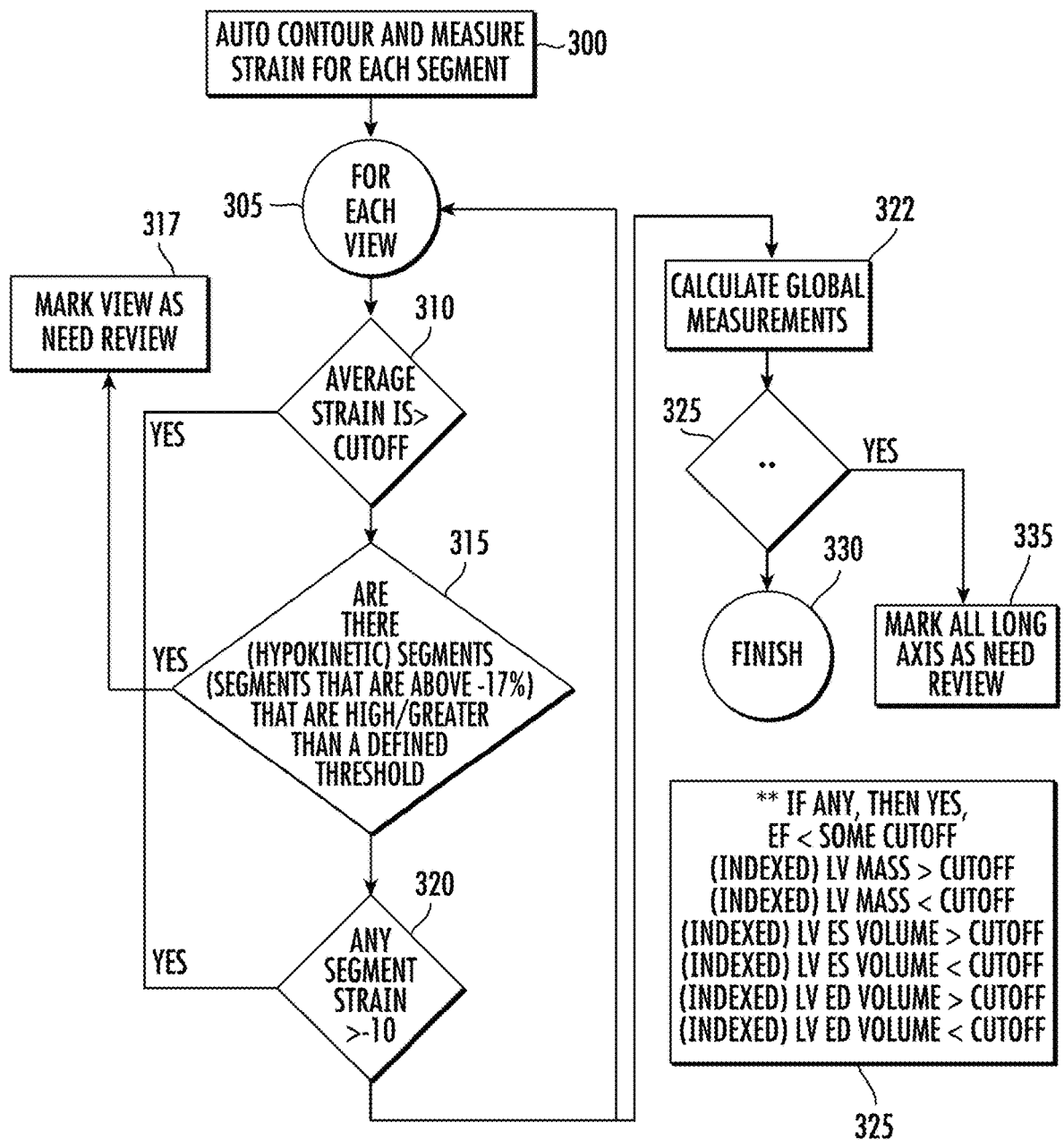
FIG. 5 is a flow chart of actions that can be carried out to detect failed or inferior segmentation to provide quality control of contouring/segmentation according to embodiments of the present invention.

Referring to FIG. 5, a flow chart of example actions for identifying segments that may need further review for a quality review/control assessment tool for confirming proper contouring and resulting segmentation to facilitate proper strain measurement quantifications is shown.

An image is contoured, segments defined, and strain measured for each segment (block 300). For each long axis view (block 305), determine whether average and/or global strain is greater than a defined cutoff (block 310); determine if there are (hypokinetic) segments (segments that are above −17%) that are greater than a defined threshold (block 315); and determine if any segment has a strain value that is greater than −10% (associated with akinetic or dyskinetic segments) (block 320). If any of these criteria are met (e.g., yes), then identify or flag the associated view for contour review (block 317). An example defined average or global strain cutoff is: −17%. An example defined cutoff for hypokinetic segments is 9.

Global measurements can also be calculated (block 322). If any defined criteria of the global measurements are met, then identify or flag one or more (optionally all non-manually reviewed) long axis views as needing contour review (block 325). If not, the contouring overview is complete (block 330).

The global measurement criteria can include one or more of the following parameters. Whether:

EF (ejection fraction)<a defined cutoff; (Indexed) LV Mass>a defined cutoff; (Indexed) LV Mass<a defined cutoff; (Indexed) LV ES Volume>a defined cutoff; (Indexed) LV ES Volume<a defined cutoff; (Indexed) LV ED Volume>a defined cutoff; and (Indexed) LV ED Volume<a defined cutoff. ES refers to end-systolic; ED refers to end-diastolic; indexed refers to values divided by body surface area to normalize values to body habitus.

Representative lower and upper cutoffs for LV mass index are 39 and 75 g/m$^2$, LV ED volume index are 53 and 99 ml/m$^2$, and LV ES volume index are 15 and 40 ml/m$^2$ respectively.

Embodiments of the invention can electronically review image generated topological shapes of the contours associated therewith to identify poor or bad segmentation. Embodiments of the invention can configure the module 10M (FIGS. 2A-2C) to carry out this review.

Embodiments of the invention can configure the module 10M (FIGS. 2A-2C) to evaluate whether there is likely to be poor segmentation directly from the images using defined image quality attributes. This includes the assessment of the image signal-to-noise ratio and the planning of the images as determined from the DICOM header.

Embodiments of the invention can configure the module 10M (FIGS. 2A-2C) to employ Artificial Intelligence (AI) and/or machine learning to determine the quality of the images and clinical usefulness and/or poor contouring and resulting segmentation. The SENC images have in them the encoding of the imaged tissue with strain, which quantifies the deformations undertaken by that tissue. In the case of the heart, the deformations are caused by the normal function of the heart muscle during contraction and relaxation to pump the blood. The nature of the SENC images provides a unique set of features useful for any training goal based on AI and/or machine learning. In particular, quantitative strain data within the myocardium for the SENC images throughout a single cardiac cycle provides definitive information that can be used with machine learning, deep learning and/or artificial intelligence techniques to provide automated contouring, quality control of imaging, fingerprinting for clinical diagnosis, titrating/customizing medical management, and identifying progressive changes in function due to cardiac disease progression, toxicity from cancer treatment, cardioprotection of diseases or cardiotoxicity, and response to interventional procedures. The benefit from applying machine learning, deep learning, and/or artificial intelligence from quantitative data versus having to interpolate information before applying such techniques is improved accuracy and clinical utility.

Embodiments of the invention can configure the module 10M (FIGS. 2A-2C) to generate the SENC images and use machine learning to automatically contour the tissue of the epicardial and endocardial surfaces for boundary edges of the myocardium. Strain provides a unique marker of deforming tissue, which is contracting heart tissue, in the SENC images. This is especially true for high tuning images that show fully contracted myocardium and filters static, undeformed myocardium. Therefore, machine learning can be used to efficiently and accurately separate myocardial tissue of the heart from all other tissues of the body, which are static at rest while the heart is in motion contracting and relaxing throughout the cardiac cycle.

Embodiments of the invention can configure to module 10M (FIGS. 2A-2C) to employ free navigational image data acquisition. Multiple image plane acquisitions, each in no more than a single heartbeat, can be used to provide a volume capturing of the shape and deformation of the heart during a cardiac cycle. In this case, image planes can be obtained from a plurality of slices that vary in location and orientation, which use the DICOM header information and the strain movies, and complete information of the heart muscle to construct a 3D model of contraction. Provided the machine learning used in identifying the location and extent of cardiac tissue and function, a complete 3D picture is built; where some regional information may be lacking, the MRI scanner can be instructed to obtain the image data from image planes that cover the missed regional data to fill the gap in information.

Considerations of the free navigational acquisitions

Determining the Heart's Position During the Breathing Cycle

Due to breathing, the heart moves in the vertical direction following the motion of the diaphragm. The acquisition of specific planes should take into consideration the location of the heart according to breathing. This is especially critical in horizontal imaging planes as the heart moved through the plane with breathing. This is especially clear in the 4-chamber view of the heart. It is important then to pick a fixed point in the breathing cycle to image the heart. Because of the rapid acquisition of SENC using the MyoStrain® MRI imaging system, repeated acquisition can be performed to know the motion of the heart during breathing.

Determining the Position of the Acquisition Plane From DICOM Metadata

From the DICOM header, the imaging plane position and orientation is known. Moreover, from the DICOM images the positioning of the patients during the exam/scan can be known including whether the patient was placed head-first, or feet first, and whether the patient on the lying on the back, side, or front. By having this information, the actual location of the heart can be determined in the acquired images and auto segmentation, then these planes can be mapped into 3D to know the exact view of the heart.

Determining the Exact Position and Shape of the Heart in the Acquired Movies Using the auto contouring, the location of the heart chambers on the image plane (the movie) is determined. This can help in relating the position of the different views to the cardiac anatomy, and, hence, identify imaging views that are not well planned.

Embodiments of the present invention can configure the module 10M (FIGS. 2A-2C) to use AI and/or machine learning to provide instructions to an MRI clinician to improve image quality and/or contouring and segmentation. Based on the SENC images, the contouring methods and/or the quality assessments discussed above, specific instructions can be provided to operators of the MRI scanner to correct imaging parameters, including the proper location and orientation of the SENC images for improved diagnostic or prognostic results.

The Right Long- and Short-Axis Planes

The instructions can be electronically generated by the module 10M (from the software) to provide the user with the guidance to plan the right long- and short-axis views of the heart. The instructions can point to important features of the observed anatomy and the required handling of the imaging planes to obtain the correct strain values.

Embodiments of the invention can use AI/machine learning for image quality assessment. For example, the quality of the SENC images can be evaluated using AI/machine learning. The assessment of the quality can determine whether the (auto) segmentations are acceptable or deficient. In case of predicting deficiency and/or contouring/segmentation failure the module 10M (FIGS. 2A-2C) can notify the user and terminate the use of the corresponding (auto) segmentation.

The free navigational embodiments, described above, are able to rapidly create a 3-dimensional model of contraction without image planning except to identify at least one reference point of the heart from which multiple planes intersection to get a comprehensive map of the strain throughout the heart. After defining this at least one reference point, which may comprise the atrioventricular connection that centers the right and left atrium to the right and left ventricle, mid-ventricular septal point, and/or other location of the heart, the MRI scanner may be instructed to obtain multiple SENC image sequence movies, each within a single cardiac cycle, at a plurality of image planes that intersect the at least one reference point. The plurality of SENC image sequence movies are then integrated together into a 3-dimensional model that may be later sliced into defined image planes (e.g. basal-, mid-, apical-short axis, and 2-chamber, 3-chamber, 4-chamber long axis). Avoiding the need for image planning except defining the least one reference point avoids operator error in defining out-of-plane images and extensive timing for operators to accurately choose image planes. In addition, free navigational imaging minimizes the impact of patient movement during imaging because the integration is able to detect and accommodate for that movement.

In the current free navigational embodiment that produces 3-dimensional models of intramyocardial strain that may be later sliced into defined image planes, 15 to 100 free navigational image sequences defining 20 to 100 planes may be integrated. This free navigational imaging may be augmented to ensure longitudinal strain is adequately represented by including more than one reference point. For example, 3 or more left ventricular septal locations may be utilized to improve the accuracy of 3-dimensional strain mapping and ensure longitudinal intramyocardial left ventricular strain is directly measured at least along the basal, midventricular, and apical regions of the heart.

Since each image plane requires a single heartbeat, more than 100 free navigational image sequences may be acquired to increase the spatial resolution and improve interpolation when developing the 3-dimensional model. Of course, more image sequences require increased post-processing power which may increase the processing time and expense of computing power required to process, analyze, and display the 3-dimensional model.

Figure 6A:
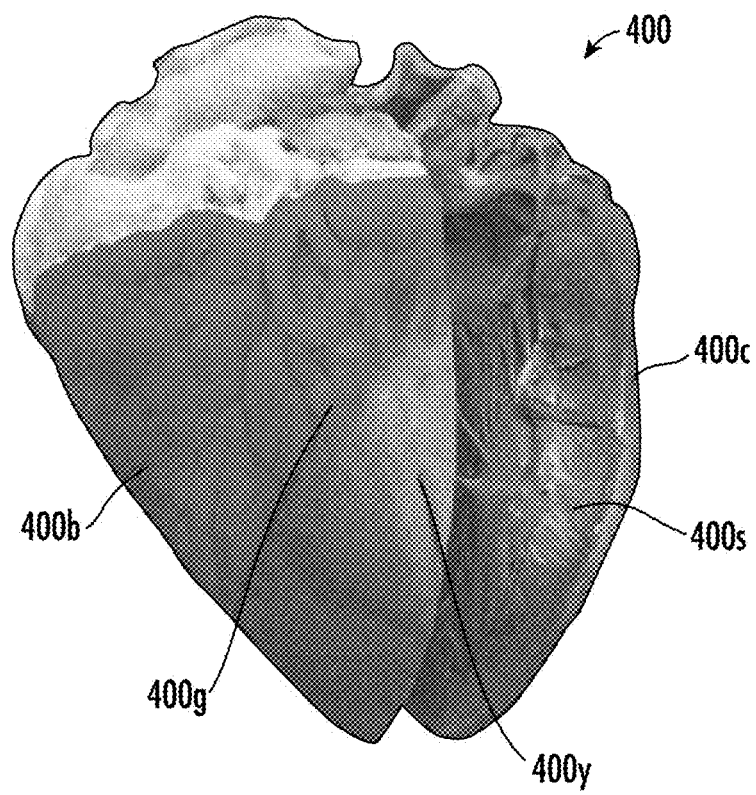
FIGS. 6A-6C are 3-dimensional models with integrated measurements of strain that visually indicate locations of dysfunction and/or changes in function, which can be used serially at different or across exam intervals, according to embodiments of the present invention.
Figure 6B:
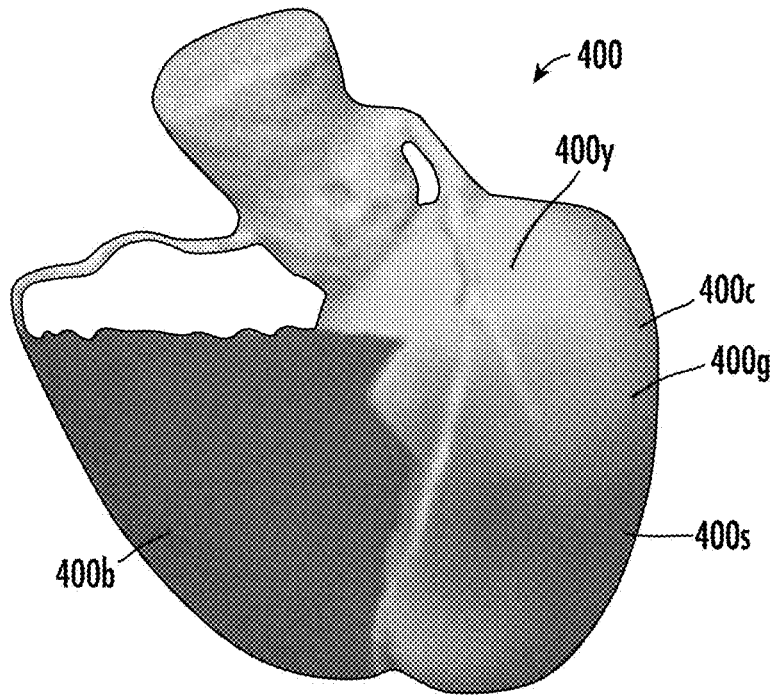
Figure 6C:
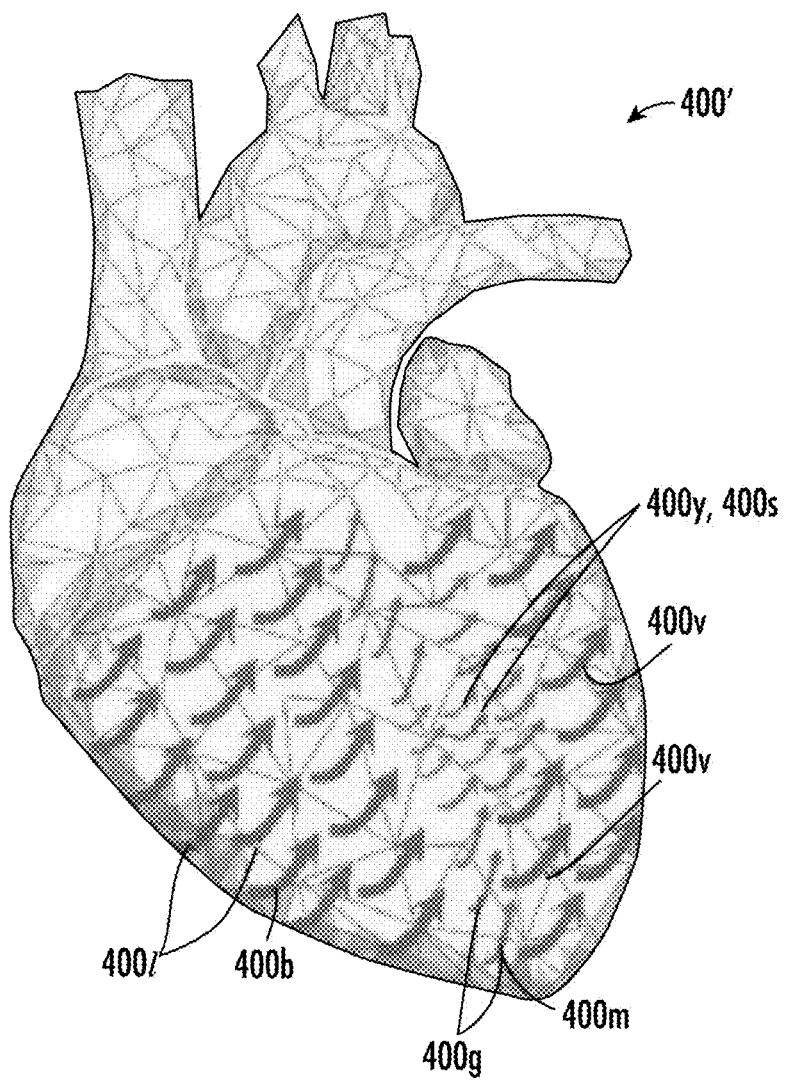

Referring now to FIGS. 6A-6C, embodiments of the invention can integrate strain measurements onto/into a 3D (predefined and standardized, or based on actual heart dimensions for the target patient) model of the heart 400 to visually illustrate locations and extent of myocardial dysfunction. The model 400 can provide visualization(s) at different points in time of a cardiac cycle and/or provide a cine of visualizations of strain propagation pattern in 3D over a cardiac cycle. The model 400 can be provided as a standardized model of a corresponding patient population (based on age, gender and the like). The model 400 can alternatively be customized to reflect a corresponding size and shape of a particular patient using patient image data.

As shown in FIGS. 6A and 6B, a standardized or defined color-coded scale 400c of strain values 400s may be used. The color coding 400c and scale 400s may correspond to those shown in the two-dimensional graph of FIG. 7 in U.S. Pat. No. 10,524,687, which may be utilized to differentiate strain throughout the 3-dimensional model, the contents of which are hereby incorporated by reference as if recited in full herein. The model 400 can illustrate different strain categories such as dyskinetic, akinetic, hypokinetic, normokinetic and hyperkinetic with each shown in different colors.

FIG. 6B shows the 3D model 400 of the left ventricle and right ventricle showing the extent of dysfunction based on the color-coded treatment scale 400s. In some embodiments, yellow regions 400y correspond to peak strain with myocardial contraction less than 10%, green regions 400g correspond to contraction between 10 and 17%, and blue regions 400b correspond to contraction more than 17%. It should be noted that left atrial strain, right atrial strain, aorta strain, or other muscular (cardiac or non-cardiac) tissue strain may also be measured and displayed on a corresponding 3-dimensional model.

Longitudinal and circumferential strain may be shown separately or combined into a single metric of myocardial function for the strain measurements used for the model 400. It should be noted that other image planes that don't only provide longitudinal and circumferential strain (atypical planes) may be combined to the typical longitudinal and circumferential strain obtained by short axis and long axis planes, respectively. Integrating multiple strain planes together can provide more detailed information on exact contraction profile considering each plane provides a strain vector that can be integrated from a 3-dimensional perspective to provide exact information on contraction direction and magnitude. Since SENC can obtain images in 1 heartbeat per image plane, the addition of multiple additional planes throughout the heart can still provide a rapid way to increase the detailed mapping of contraction throughout the heart.

The importance of integrating strain with different vectors into a 3-dimensional model is because of evidence of helical and circumferential myocardial fiber architecture as discussed by Buckberg G D, et al (Buckberg G D, et al. What is the heart? Anatomy, function, pathophysiology, and misconceptions. Journal of Cardiovascular Development and Disease. 2018; 5:33. Doi:10.3390/jcdd5020033). Observations that the heart contains clockwise and counterclockwise helical and circumferential fibers explain why longitudinal and circumferential vectors (optionally as well as other plane vectors, if needed) can be important to determining heart health based on the strength of contraction. This may be especially important because the orientation of fibers varies across the thickness of the heart and throughout the length and circumference of the heart.

Changes in contraction health, both regional and global, due to cardiac diseases, toxic response to pharmaceutical agents, improvement based on cardioprotective medications, surgery for cardiac ailments, or other cause of cardiac dysfunction or improvement in function benefit from displaying longitudinal and circumferential strain individually and combined as a single metric of contraction. Monitoring the changes (worsening or improving) in cardiac contraction strength based on longitudinal and circumferential strain helps diagnose and manage cardiac diseases, impact of diseases on heart health, as well as response to pharmaceutical drugs whether due to toxicity, cardioprotection, or adverse inter-drug reaction.

Peak strain may be the metric that is shown in the 3-dimensional model 400. Alternatively, systolic or diastolic strain rate may be projected on the 3-dimensional model. Duration of peak strain may also be illustrated. Midmyocardial strain (peak strain, strain rate, duration of peak strain, time to peak strain, or other strain metric) may be shown; alternatively, endocardial or epicardial strain may be illustrated.

Alternative illustration techniques besides purely color-coded visuals of strain metrics may be used to show not only the magnitude of contraction but the direction of contraction. For example, when combining the longitudinal and circumferential strain, visual vectors 400v, optionally arrows, representing the resulting direction of contraction with size and/or color of the vector 400v signaling the magnitude of contraction may be used as shown in FIG. 6C. These visual vectors 400v may also be provided in different thickness and/or color coded based on magnitude to better visually represent strain metrics (peak strain, strain rate, duration of peak strain, time to peak strain, or other metric). The embodiment in FIG. 6C shows the model 400' with large visual vectors 400l (shown in blue 400b) representing midmyocardial peak contraction better than 17%, medium visual vectors 400m (shown in green 400g) representing peak contraction between 10 and 17%, and small visual vectors 400s (shown in yellow 400y) representing peak contraction worse than 10%. The small and medium visual vectors 400s, 400m, respective, can have a smaller width and length than the large visual vectors 400l. The visual vectors 400v can change size and direction between visualizations based on timing within the cardiac cycle. The visual vectors 400v can be provided as arrows (single or double ends in opposing directions), contraction lines or other visual vector shapes and may be utilized with thickness defined by strain metric magnitude and line direction defined by integration of longitudinal and circumferential strain metrics (atypical plane strain metrics may also be integrated).

Topographical maps that integrate peak strain and strain rates into a single 3-dimensional map be also be shown to demonstrate the importance of strain magnitude as well as rate of change in strain during the cardiac cycle.

The 3-dimensional model 400, 400' may include only the left ventricle as shown in FIG. 6A or may include the right ventricle as shown in FIG. 6B that may be electively hidden to better highlight the septal left ventricular function and then unhidden to visually observe regional strain measurements for the right ventricle. Alternatively, left and right atrium may be included; ascending aorta, aortic arch, and/or descending aorta may also be included as well as any cardiac anatomy with muscle that contracts in response to a stimulus. The standard left and right ventricular shapes (as well as atrial shapes, aorta, and other anatomy if desired) can be adjusted in size and shape based on the traditional measurements of the volumes, mass, and wall thicknesses to associate hypertrophy, ventricular dilatation, and other anatomic identifiers of diseases to function based on strain. For temporal information about strain propagation, 3-dimensional maps can be cycled to reflect strain metrics throughout the cardiac cycle. This propagation may be displayed as a movie to identify dyssynchrony, prolonged contraction, abnormal contraction or otherwise altered conduction. Alternatively, the temporal information may be summarized into composite values (e.g. strain rate, time to peak strain, activation time to initiation of contraction, duration of peak strain, etc.) and displayed on static 3D models. The 3-dimensional maps or models can be created to express the variations of contraction patterns according to the underlying pathology. Example of these temporal maps or models are:

A 3-dimensional temporal map or model can be configured to show the time differences for different regions of the heart on reaching the maximum contraction (peak strain), e.g., peak contraction delay. This time-to-peak contraction map or model can visually identify and/or highlight dyssynchrony attributed to left bundle branch block, right bundle branch block, other conduction abnormality, cardiotoxicity, or other cause of dyssynchronous contraction.

A 3-dimensional temporal map or model can be configured to show the delay in the start of regional contraction at the onset of systole, e.g., initiation of contraction delay. This time to initiation of contraction map or model can visually identify and/or highlight dyssynchrony or delayed contraction similar to the peak contraction map or model.

A 3-dimensional temporal map or model can be configured to show dyssynchrony in the rate of relaxation and/or prolonged duration of peak contraction during diastole, e.g., regional variations in relaxation pattern. This time of peak contraction map or model can visually identify and/or highlight regions of the heart that maintain peak strain for long periods of time to accommodate for increased afterload or vascular resistance. When the heart contracts against increased resistance, myocardium must preserve peak contraction to account for a delay in blood pumping through the vasculature.

A 3-dimensional temporal map or model can be configured to show the extent and/or speed of propagation of contraction from end systole to end diastole. This propagation rate map, e.g., transmural propagation rate map, can show activation of contraction during systole, duration of peak contraction, and relaxation during diastole to evaluate the ability of the heart to contract in a normal, synchronous manner to efficiently pump blood. Propagation rate models can incorporate systolic strain rate, time of peak contraction, diastolic strain rate, time of relaxation, or a composite of two or more of these rates that can be displayed on a respective 3-dimensional model 400, 400'. These propagation maps or models can be useful to help evaluate progression of cardiac diseases, cardiotoxicity from cancer treatment(s), ischemia by observing changes with stress testing, and/or impact from cardioprotective therapies or interventional procedures.

Risk Scores

Integrating longitudinal and/or circumferential strain measurements (and atypical plane strain measurements optionally) into at least one risk score can be important to help physicians and patients more readily interpret results and/or monitor changes based on disease progression, and pharmacological or interventional treatments.

Previously, as discussed in co-assigned U.S. Pat. No. 10,524,687, the ability to measure strain, which is a measure of tissue deformation, was discussed. In case of monitoring the health of the heart, it is contemplated that integrating measurements of strain, for example, two components of strain (longitudinal and/or circumferential), into a risk score can provide an important assessment of cardiac health status and/or an assessment tool to monitor changes in heart health over time.

One way to facilitate understanding of the clinical findings from strain measurements is to provide a risk score that encompasses key features that can differentiate progressive change in function due to risk factors, diseases, and therapeutic options.

Based on the current two plane orientations, long-axis and short-axis, strain is measured in the circumferential and longitudinal directions, respectively. SENC strain is measured perpendicular to the image plane which is why the long-axis planes (2-chamber, 3-chamber, and 4-chamber) provide circumferential strain and the short axis planes (basal-, mid-, and apical-short axis) provide longitudinal strain. It should be noted that other planes may be used and integrated together to provide more detailed information on exact contraction profile from a 3-dimensional perspective. Since SENC can obtain images in one heartbeat per image plane, the addition of multiple additional planes throughout the heart can provide a still rapid way to increase the detailed mapping of contraction throughout the heart.

Peak strain values represent one important health metric of the myocardium as discussed in U.S. Pat. No. 10,524,687, incorporated by reference herein, especially considering peak strain is less dependent on patient characteristics such as age and gender than other strain metrics such as strain rate.

Measurements of longitudinal and/or circumferential strain and/or the relation between these metrics can be used to characterize the health of the myocardium.

In some embodiments, a relationship between longitudinal and circumferential strain components of contraction can provide a clinical characterization of cardiac health status, such as the health, or lack of health, within a small segment (s) of tissue and/or globally.

One example of such a relationship could be a weighted ratio between the peak segmental strain values. Normal tissue is expecting mostly equal values of the two (longitudinal and circumferential) components based on midmyocardial measurements. In case of some diseases, such as hypertrophic cardiomyopathy, the value of midmyocardial longitudinal strain is significantly lower than that for midmyocardial circumferential strain. In other cases, such as hypertensive heart disease, circumferential midmyocardial strain declines before longitudinal. The weighted ratio may treat circumferential and longitudinal strain equally or reflect that, in many diseases, circumferential strain has been proven to predict of risk of heart failure (Choi E Y, et al. Prognostic value of myocardial circumferential strain for incident heart failure and cardiovascular events in asymptomatic individuals: the Multi-Ethnic Study of Atherosclerosis. European Heart Journal. 2013; 34:2354-2361).

No matter the ratio and whether the weighted ratio is constant throughout the heart or regionally dependent, both circumferential and longitudinal strain measurement components can be included in a risk score calculation according to some embodiments of the present invention. A weighted ratio may be used to understand the impact of diseases and/or pharmaceutical agents on the natural contraction pattern.

In some embodiments, a risk score $R_s$ can be calculated as a weighted ratio of a number $N_1$ of (global or regional) circumferential or longitudinal or circumferential and longitudinal segments having strain in a first range (less than or equal to $-17\%$) to a number $N_2$ (global or regional) circumferential or longitudinal or circumferential and longitudinal segments having strain above the first range: $N_1/N_2$ or $N_2/N_1$. Optionally, the ratio can be provided as a weighted ratio of $XN_1/N_2$, $XN_2/N_1$ or $XN_1/YN_2$, where X is a defined weight and, where used, where Y is a different defined weight. X and Y can be a weight less than 1 and greater than 0 or greater than 1 and less than 100. Alternatively, the weighted ratio can be provided as $XN_1/(N_1+N_2)$ to evaluate the percent of normal contracting myocardium; it may also be evaluated as the percent of abnormal myocardium based on $XN_2/(N_1+N_2)$ To evaluate the effects of diseases and/or pharmacological agents on cardiac function, more granular measurements and integration of longitudinal and circumferential strain components beyond peak midmyocardial strain can be used to enhance diagnosis and management because it will better account for the complex helical and circumferential myocardial fiber architecture as described by Buckberg G D, et al (Buckberg G D, et al. What is the heart? Anatomy, function, pathophysiology, and misconceptions. Journal of Cardiovascular Development and Disease. 2018; 5:33. Doi: 10.3390/jcdd5020033). Considering the heart contains a plurality of clockwise and counterclockwise helical and circumferential fibers interspersed throughout the myocardium, integrating intramyocardial longitudinal and circumferential strain vectors throughout the thickness of the myocardium will better reflect the impact of diseases and management regimens on the function of the heart.

SENC's unique ability to directly measure intramyocardial deformation perpendicular to the image plane enables pixel-by-pixel quantitative strain measurements. As discussed above, intramyocardial longitudinal and circumferential strain vectors (peak strain, strain rate, duration of peak strain, time to peak strain, or other strain metric) may be integrated on a pixel-by-pixel basis and applied to 3-dimensional models to better reflect contraction profile throughout the cardiac cycle.

The myocardial wall may alternatively be separated into thirds (endocardial, midmyocardial, and epicardial) or other fractional layers to simplify calculations of integrated strain vectors. To increase accuracy of disease diagnosis and/or management efficacy, integrating longitudinal and circumferential strain for each layer (e.g. endocardial, midmyocardial, and epicardial), across layers, and/or between individual layers based on weighted ratios, averages, or other calculation provides more quantitative data that machine learning, deep learning, and/or artificial intelligence techniques can apply. Alternatively, a subset of these metrics can be integrated into a single risk score or a multitude of risk scores or parameters which together can assist in diagnosing cardiac diseases, analyzing the impact of diseases on progressive changes in function, monitoring the safety and efficacy of pharmaceutical medications, and evaluating the impact of interventional procedures on the performance of the heart, for example.

An example risk score (which, when provided or authorized to be provided by Myocardial Solutions, Inc., can be identified as a MYOHEALTH™ risk score which may be provided by the MyoStrain® MRI system) calculates the percent of normally contracting myocardium from a composite percentage of a defined number of longitudinal left ventricular segments (typically 16 segments: 6 basal-, 6 mid-, and 4-apical short axis) and a defined number of circumferential left ventricular segments (typically 21 segments: 7 two-chamber, 7 three-chamber, and 7 four-chamber long axis) that have midmyocardial peak strain$\leq-17\%$.

$$\text{Risk Score} = \frac{\left(\begin{array}{c}(\text{\# Longitudinal Segments} \leq -17\%) + \\ (\text{Circumferential Segments} \leq -17\%)\end{array}\right)}{\text{Total \# of } LV \text{ Long. and Cir. Segments Analyzed (e.g. 37)}} \quad \text{EQUATION 2}$$

The result can be multiplied by 100.

Figure 7:
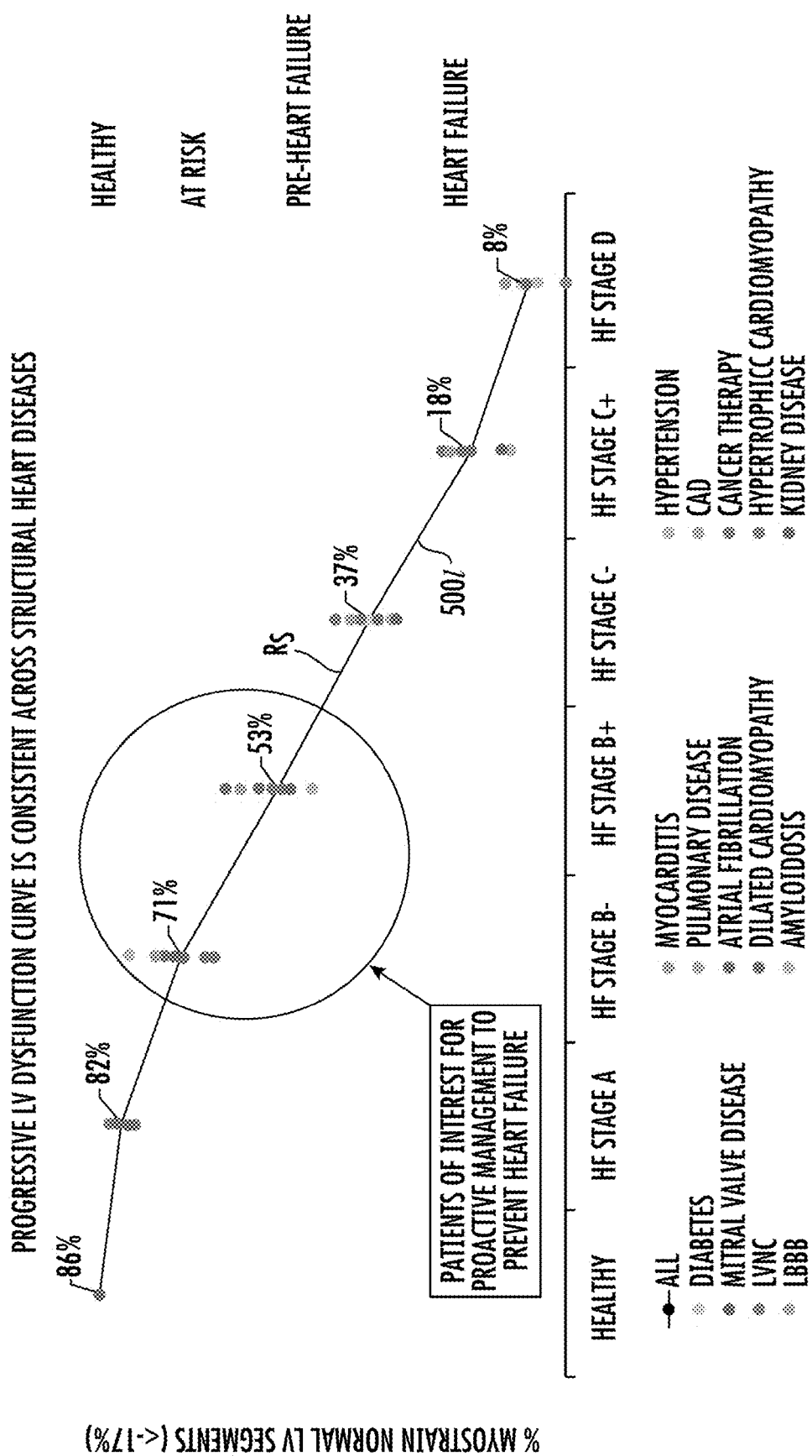
FIG. 7 is a graph of a risk score of percent of left ventricle (LV) segments having normal strain measurements versus dysfunction that can identify healthy to different stages of heart failure that can provide information regarding a potential progression (or regression) of heart failure according to embodiments of the present invention.

It is also contemplated that Equation (2) can be modified as the inverse so that the composite summation is the denominator which will make the risk score the inverse of the example shown in FIG. 7.

In an example embodiment, as the risk score $R_s$ declines, structural heart disease increases and the ability of the heart to compensate for regional dysfunction to maintain cardiac output diminishes. FIG. 7 shows the relationship between the $R_s$ risk score calculated using Equation (2) and progression of heart failure based on modified ACC/AHA criteria of heart failure from Myocardial Solutions' clinical data registry database of 1710 scans in 1352 patients.

ACC/AHA Heart Failure Classification

Stage 0: Healthy patients without major risk factors
Stage A: Patients at risk for heart failure who have not yet developed structural heart changes (i.e. those with diabetes, those with coronary disease without prior infarct)
Stage B: Patients with structural heart disease (i.e. reduced ejection fraction, left ventricular hypertrophy, chamber enlargement) who have not yet developed symptoms of heart failure
  B-} HF Stage B with lower degree of structural heart disease
  B+} HF Stage B with higher degree of structural heart disease
Stage C: Patients who have developed clinical heart failure
  C-} HF Stage C with lower degree of structural heart disease
  C+} HF Stage C with higher degree of structural heart disease
Stage D: Patients with refractory heart failure requiring advanced intervention (i.e. biventricular pacemakers, left ventricular assist device, transplantation)

As shown in FIG. 7, the risk score Rs provides a linear relationship 500*l* with various stages of heart health from healthy/normal to different heart failure stages including A-D, with heart failure states A-B+ associated with an at-risk and/or pre-heart failure status of particular clinical interest for proactive management to prevent clinical (typically irreversible) heart failure. The range for proactive management can be between about 75% to about 50%.

Other calculations of a risk score may be used to quantify heart health. For example, while Equation (2) above uses a risk score calculated using midmyocardial strain, other risk scores may focus on endocardial or epicardial strain with normal contraction based on the ≤−17% threshold. A functional risk score based on a different threshold, such as a threshold of −10% instead of the ≤−17 threshold may also be utilized to evaluate the percent of functional myocardial contraction as opposed to the percent of normal myocardial contraction.

Alternatively, a risk score $R_s$ may be based on systolic or diastolic strain rate, duration of peak strain, time to peak strain, or other strain metric in terms of comparison to a defined threshold, and may be calculated as a weighted average or ratio, or calculated with another equation from actual values that incorporates both longitudinal and circumferential values in the calculation.

It should also be noted that multiple risk scores, including those derived from third party tests such as biomarkers (e.g. Troponin, BNP, etc.), may be integrated together or included as a multiparametric analysis tool that may help evaluate diseases and management performance. For example, endocardial, midmyocardial, and epicardial risk scores calculated similar to Equation (2) or the ratios discussed above may be combined or used in concert to identify diseases that have subtle differences in which fingerprinting for diagnosing the disease is improved with a plurality of features. Alternatively, one or more risk scores based on different criteria including a risk score that is based on two or more of peak strain, systolic strain rate, diastolic strain rate, duration of peak strain, and/or time to peak strain may be combined into a single value or matrix of values that fingerprint diseases and extent of dysfunction to monitor the impact of management and/or prevention.

While the example risk score embodiment described above with respect to FIG. 7 uses 37 left ventricular segments, other risk scores may benefit from segmenting the left ventricle (both long axis and short axis) into many more segments, n>37 such as 40<n<200 to get a more accurate value of the percent of normally contracting myocardium. Of course, this enhanced segmentation may apply to any risk score based on SENC direct measurement of intramyocardial strain perpendicular to the image plane. In addition, or alternatively, right ventricular, left atrial, right atrial, and/or aortic strain metrics (strain measurements from segments thereof) may also be included in a risk score.

Combined Rest and Stress Risk Scores

Risk scores, described above, can enhance their clinical value when comparing or integrating rest and stress conditions. For example, evaluating ischemic coronary artery disease or diseases that cause microvascular obstruction may benefit by combining metrics related to a change in rest vs stress strain metrics to define whether function declines consistent with identification of ischemia consistent with a critical stenosis in ischemic coronary artery disease, or a wide enough region in which microvascular obstruction impairs long-term heart health.

This comparison during stress testing may be performed during pharmacological stress testing using vasodilators (e.g. Adenosine, Regadenoson, etc.), direct-acting agents that increase contractility (e.g. Dobutamine), exercise, and/ or breathing maneuvers (e.g., Valsalva maneuver, hyperventilation, etc.). While the risk score(s) may be compared between rest and stress conditions on a global basis, a single risk score may be developed by comparing segmental changes, and/or multiple segmental risk scores may be obtained with each region identifying a likelihood of ischemia, whether or not these segmental risk scores are combined into a single value or analyzed separately.

Embodiments of the invention can provide at least one risk score that can detect a likelihood of early damage of muscle. That is, a risk score can be used to provide different measurements indicating the segmental and global function of the heart. Of great value is measuring the extent or percentage of weakness in the heart muscle as a measure of the development of disease as described above. This can also be presented by the number of weak segments (absolute value peak strain less than 17%) or very weak segments (absolute value peak strain less than 10%).

Figure 8:
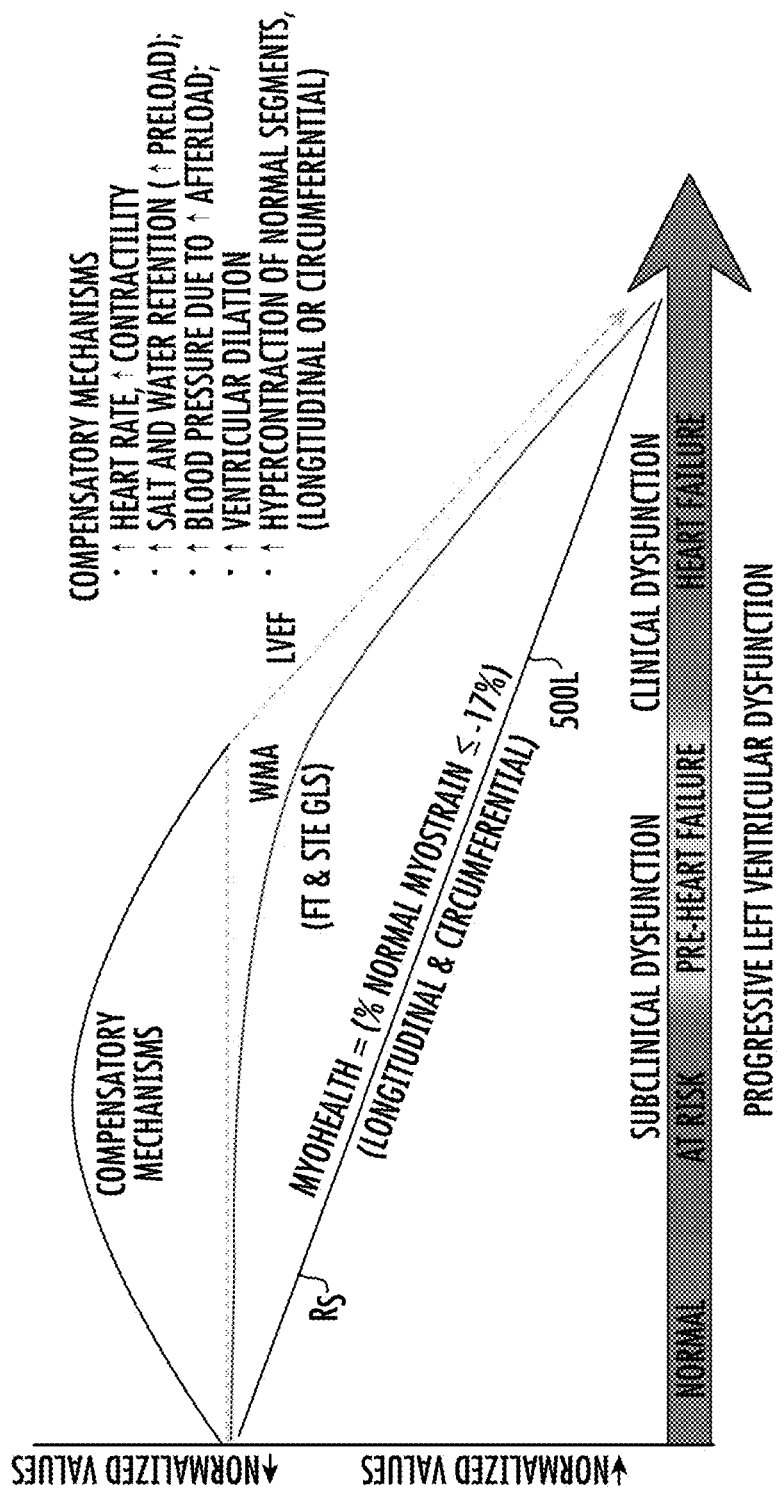
FIG. 8 is a graph of a risk score (low to high) versus progressive left ventricular dysfunction relative to impact of compensatory mechanisms on conventional measurements to thereby identify subtle changes in heart health according to embodiments of the present invention.

Many diseases of the heart progress slowly, and their effects may be identified early by regional and spotty myocardial dysfunction. Because of their limited extent, the heart is capable of compensating for this regional weakness as the healthy regions of the muscle are recruited to compensate and maintain the overall cardiac global function and output. Other compensatory mechanisms such as increased heart rate, increased rate of contraction, increased preload, increased blood pressure due to increased afterload, increased ventricular dilation, and LV hypertrophy help maintain systemic cardiac function and output despite regional dysfunction and disease progression as illustrated in FIG. 8. For this reason, global measurements, such as ejection fraction and global strains measured by current imaging modalities are incapable of revealing the onset of disease until later stages when disease is more severe.

Embodiments of the invention provide risk scores $R_s$ that use strain metrics associated with intramyocardial deformation, which does not depend on epicardial or endocardial volume. These risk score(s) $R_s$ are less impacted by compensatory mechanisms and provide a much more linear response regarding disease progression and changes in heart health due to management and/or treatment regimens. These risk scores can detect subtle changes in function before symptoms occur or conventional metrics of function identify a problem.

Figure 9:
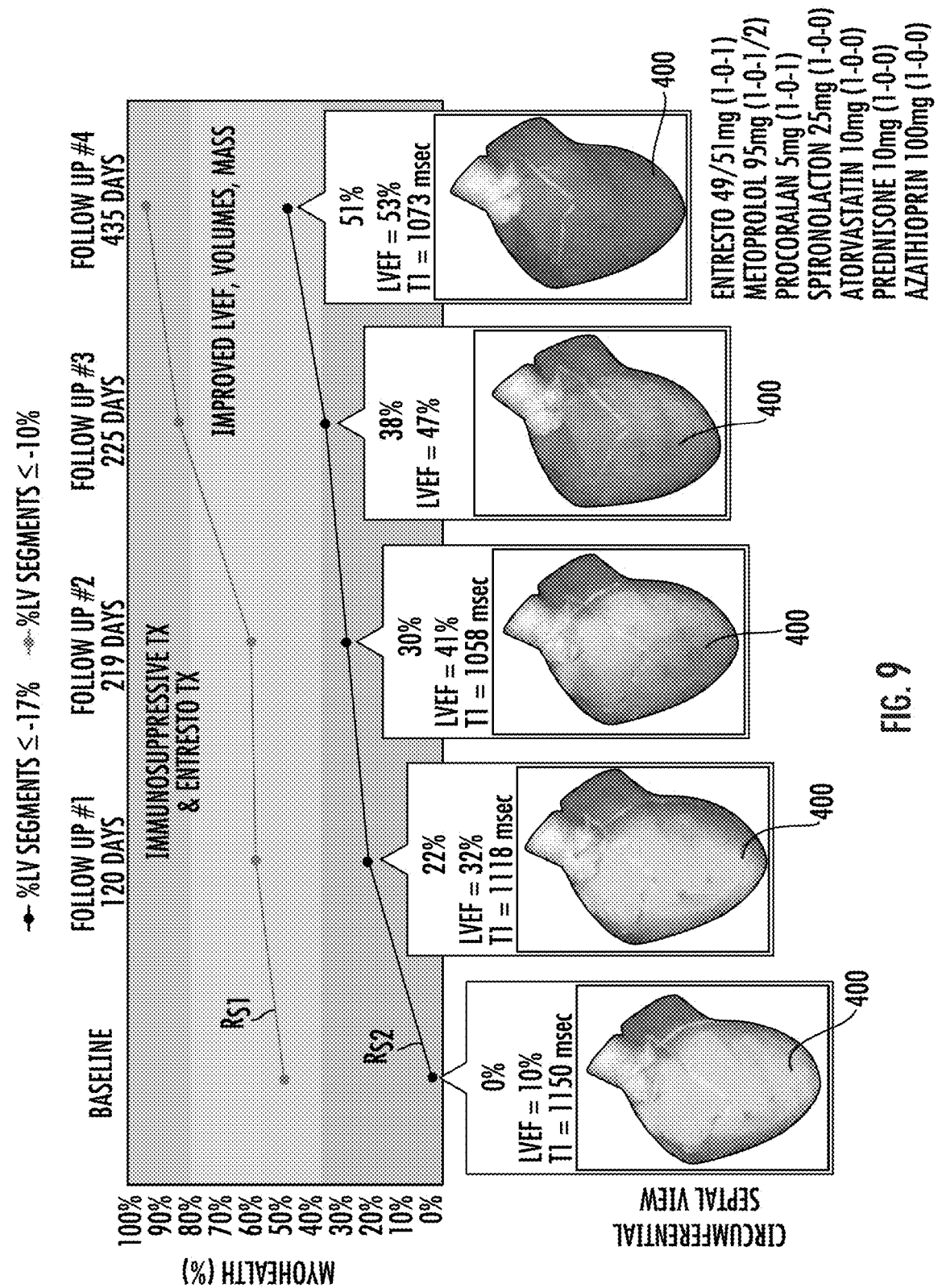
FIGS. 9-11 are graphs of a risk score reflecting a percent of normal to total strain measurements of tissue segments over time with appended three-dimensional cardiac models with integrated strain measurements illustrating changes over time based on clinical changes in heart health due to disease progression and/or management/treatment approaches.

FIG. 9 shows an example graph of changes in risk scores $Rs_1$, $Rs_2$ (e.g., % of LV≤−17%) and the percent of functional myocardium (e.g. % of LV≤−10%) in a patient with dilated cardiomyopathy, myocarditis, and symptomatic heart failure with reduced ejection fraction at baseline who gradually observed improved function in response to immunosuppressive therapy and Entresto® plus other cardioactive medications. The risk score $Rs_1$ is calculated from Equation (2) above. Risk score $Rs_2$ is calculated in a similar way as $Rs_1$ except using a different threshold, as shown the different threshold is −10%, instead of −17% as shown in Equation (2).

This example also shows circumferential midmyocardial strain metrics projected on (color-coded to) a 3-dimensional model 400 that visually show changes in regional function throughout follow-up based on a septal view of the 3D model 400.

Figure 10:
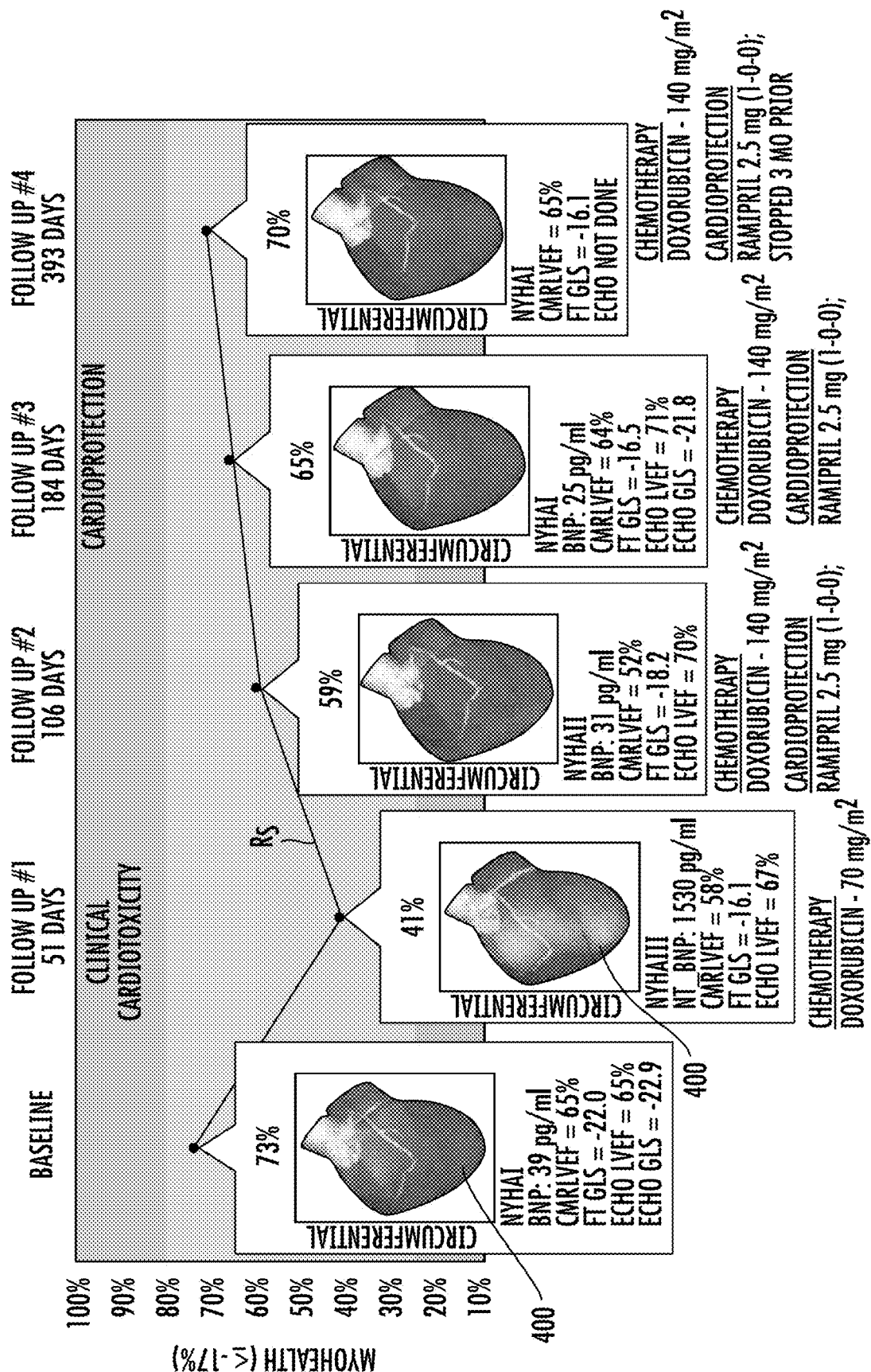

FIG. 10 shows another example in which a patient with Hodgkin's Lymphoma underwent chemotherapy and observed a cardiotoxic response in which the risk score, $R_s$, calculated as discussed above with respect to Equation (2), declined from 73% of normal contracting myocardium to 41%. This accompanied other identifiers including symptom occurrence (NYHA I to NYHA III) and biomarkers (NT-proBNP=1530 pg/ml) that identified adverse cardiac reaction to cancer treatment. Upon implementation of cardioprotective medications, the risk score $R_s$ improved back to 70% while other identifiers returned to normal. The regional changes can be observed by the 3-dimensional model 400 of circumferential peak midmyocardial strain which observed substantial septal dysfunction, which is evidenced by the substantial yellow circumferential strain at follow-up #1 which is associated with peak midmyocardial strain worse than 10% contraction. Consistent with the improvement in risk score upon successful implementation of cardioprotective medications, the 3-dimensional display of circumferential strain from a septal view returned to normal.

Figure 11:
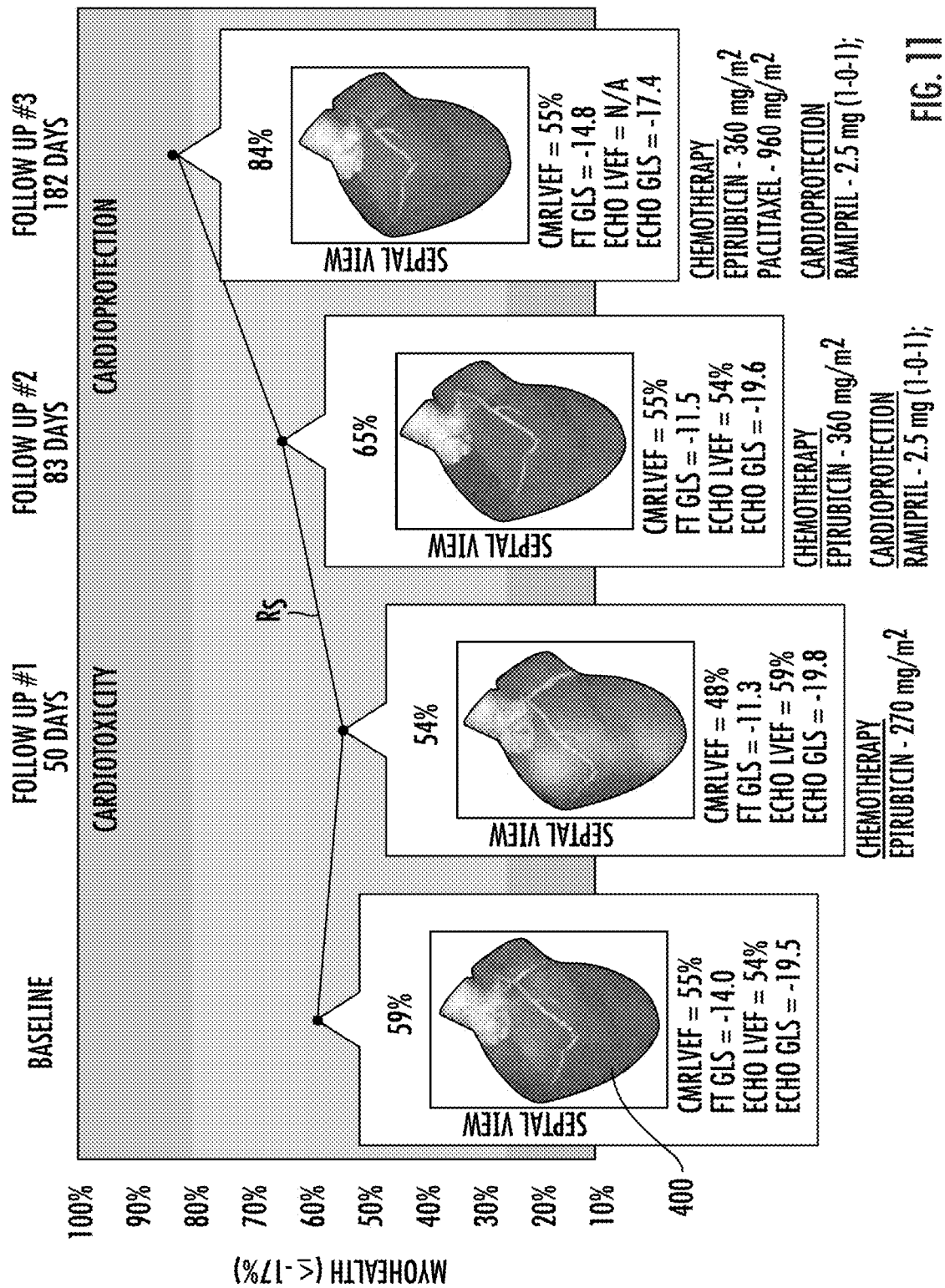

FIG. 11 shows another example of cardiotoxicity in which a patient with breast cancer had dysfunction at baseline with a risk score $R_s$ (calculated per Equation 2 above) of 59% which worsened upon administration of chemotherapy to 54%. This dysfunction was associated with substantial septal dysfunction as shown by the 3-dimensional model 400 as well as a decline in ejection fraction measured with cardiac MRI. Upon administration of cardioprotective medications, the risk score $R_s$ and regional septal midmyocardial strain returned to normal, much higher than at baseline.

Embodiments of the invention provide a risk score(s) with accuracy and reproducibility in measuring regional (segmental) intramyocardial strain which allow the detection and determination of the extent of the weaker regions in the heart muscle, even when global function is still unaffected. Therefore, the impact of diseases, therapeutic regimens, and/or ischemia can be detected early enough allowing for proper individualized medical interventions and mitigation strategies (e.g. alter treatment, prescribe heart protective medication, etc.).

It is important to mention that one or more risk scores $R_s$ can also be valuable when assessing improvement of cardiac function due to appropriate and recommended cardiac treatment. In this clinical scenario, the improvement in intramyocardial regional or segmental function will be detected earlier than observing calculating global function with current imaging modalities.

Pathological intramyocardial regional or segmental weakening of strain in certain regions will have clinical significance. These regions include but are not limited to:
Left ventricular free wall
Right ventricular free wall
Ventricular septal wall
Right ventricle (RV) insertions to the left ventricle (LV)
Layer transmurality: endocardial, midmyocardial, and epicardial
Insertions of the papillary muscles into the LV wall
Territories of coronary artery perfusion beds
Left atrium (LA) and/or right atrium (RA)
Pulmonary vein antrum
Left ventricular outflow tract
Ascending aorta, aortic arch, and/or descending aorta
Right ventricular outflow tract
Mitral valve annulus The use of MyoStrain® MRI system measurements, particularly with one or more risk scores, can provide a snapshot of the health of the heart muscle at the time of acquisition. When MyoStrain acquisitions are done periodically, at multiple intervals separated by periods of time based on the physician's guidance as part of the management of the patient, the stability of the heart or its (slow) progressive deterioration can be detected and monitored. This is especially useful in polypharmacy cases to assess patients who are treated with different medications or a plurality of interacting medications where there is a need to assess the efficacy or diverse effects of different therapeutic drug regimens including inter-drug interactions.

Embodiments of the invention can use intramyocardial segmental calculations of measurements of strain to determine the health of the myocardium using the risk score $R_s$.

Figure 12:
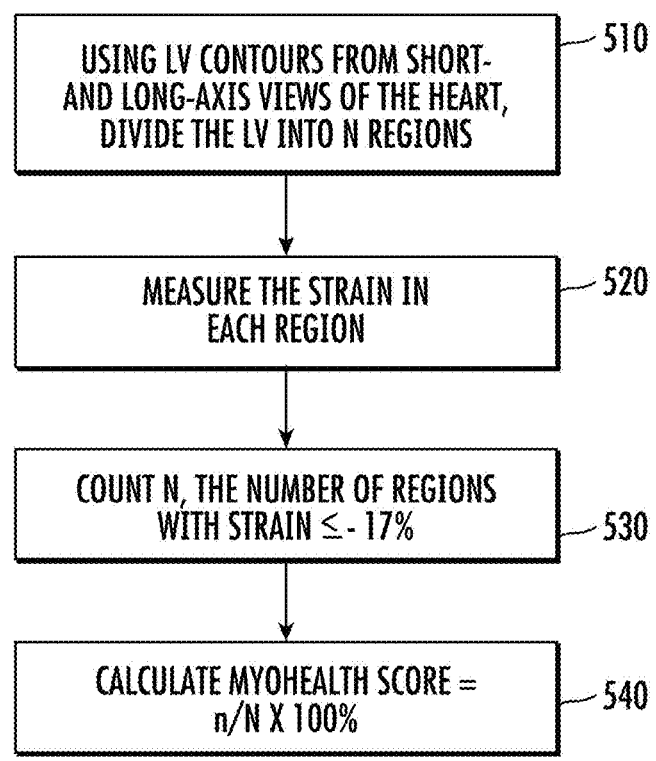
FIG. 12 is an example flow chart of actions that can be carried out to calculate a cardiac risk score according to embodiments of the present invention.

Referring to FIG. 12, example actions to calculate a risk score are described. Short and long axis MRI images f the heart can be divided/segmented into N regions using left ventricle (LV) contours (block 510). The strain in each region can be measured (directly) from the MRI images (block 520). The number n of regions having raw negative strain values ≤−17% which is associated with the percentage of the heart muscle that is contracting normally (also defined by regional segmental absolute strain≥17%) is counted (block 530). The risk score is then calculated an n/N×100 (block 540).

Figure 13:
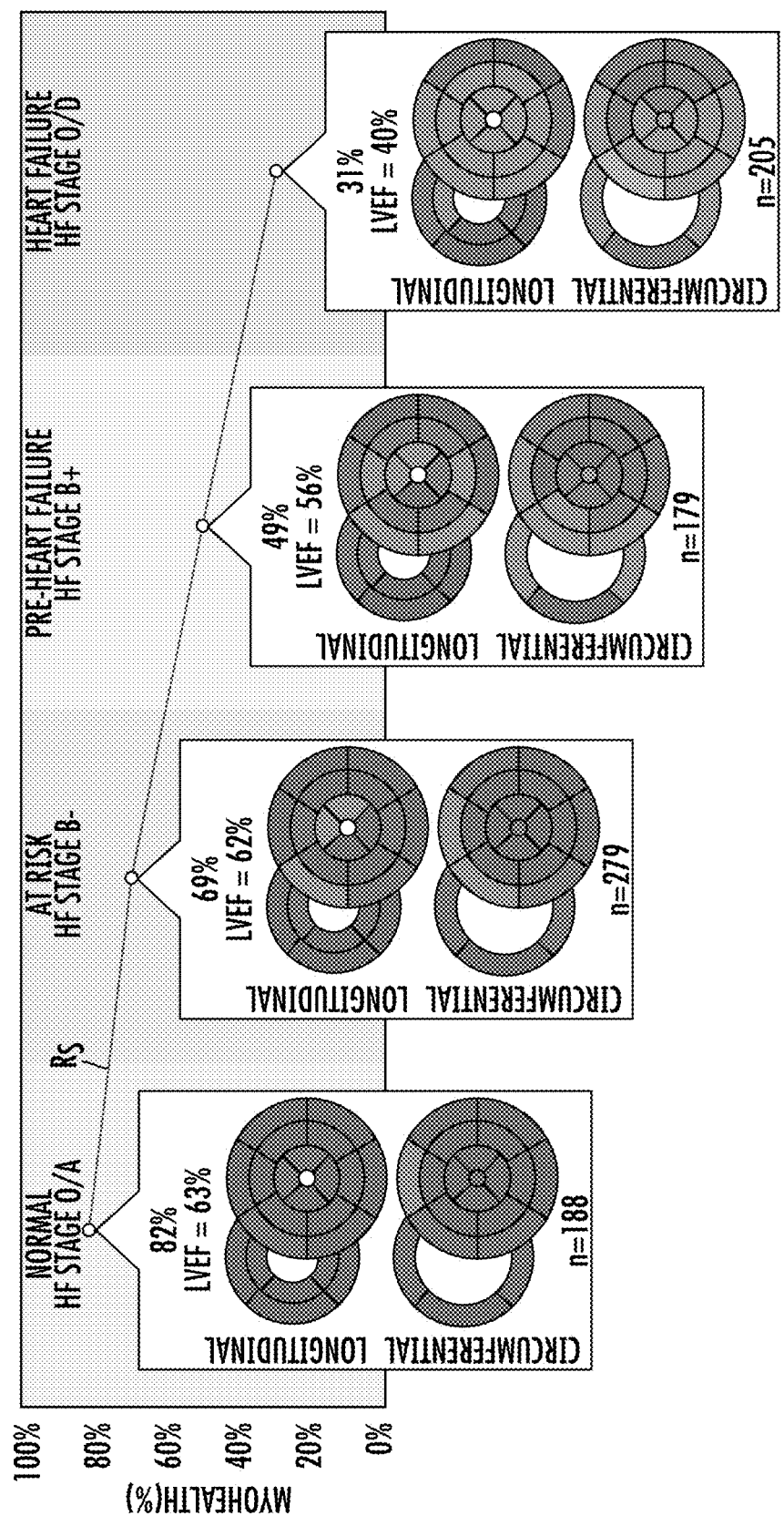
FIG. 13 is a graph of a risk score calculated as percent normal strain segments versus cardiac status with appended circumferential and longitudinal models of heart segments and LVEF percentage illustrating a linear relationship between the risk score (calculated based on segmental midmyocardial peak strain) and progression of heart failure according to embodiments of the present invention.

FIG. 13 shows the relationship between a risk score $R_s$ calculated as discussed above with Equation (2) and peak strain in segmental midmyocardial segments and segmental midmyocardial peak strain in 851 patients with arterial hypertension. Segmental strain values are color-coded as blue segments=midmyocardial peak strain≤−17%, green segments=midmyocardial peak strain between −10% and −17%, and yellow segments=midmyocardial peak strain≤−10%. As previously discussed, the risk score $R_s$ can be calculated so that it declines as structural heart disease progresses while segmental dysfunction is regionally located with the septal wall showing dysfunction earlier than other regions such as the lateral wall. In addition, in patients with arterial hypertension, septal circumferential dysfunction occurs early in the progression of the disease well before traditional metrics change or symptoms occur. Providing the ability to leverage sensitive risk scores as well as segmental and regional measurements enable early detection of changes in function due to disease progression, response to therapeutic regimens and interventions, and ischemia.

For any patient, it can be important to monitor changes in function showing changes in the segmental strain measurements of MyoStrain® MRI system numbers such as using one or more of the risk scores over periodic time intervals, as shown in FIGS. 10, 11 and 12. MyoStrain measurements, such as global, regional and/or segmental strain, as well as risk scores like the percentage of healthy regions or the number of weak segments, have been shown to be more sensitive than conventional measurements to detect subtle changes in cardiac health as described above.

FIG. 14 shows an example patient exam report 600 that provides the risk score $R_s$ and segmental peak midmyocardial strain values. Segmental graphical plots as well as the actual numbers are shown for the segmental strain values for both longitudinal and circumferential strain. The risk score $R_s$ is presented as the value and including an appended linear graph with a color-coded measurement scale to allow identification of the value relative to the health status, such as the progression curve shown in FIG. 7. The risk score $R_s$ of 43% corresponds to 16 normal LV segments divided by 37 total segments analyzed×100. The box adjacent the $R_s$ on the report 600 shows the LV segment data used for the calculation.

Figure 15:
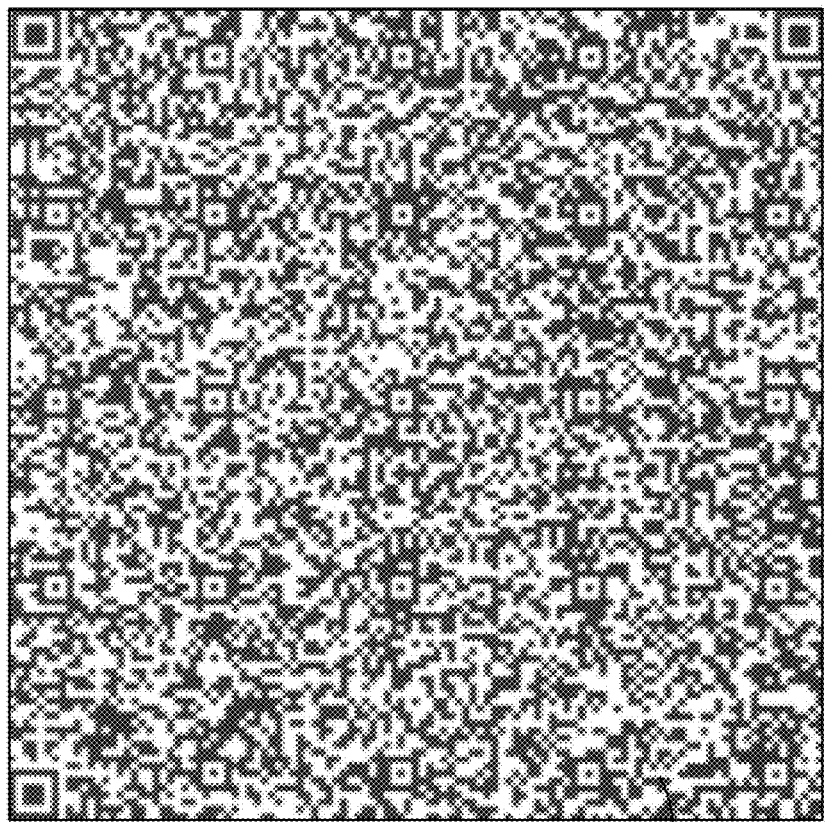
FIG. 15 is an example QR code that can provide all relevant values of the report in FIG. 14 in a manner that can be optically or electronically transferred to a mobile device, computer, or other electronic media, typically without any patient identifiers, according to embodiments of the present invention.

Data from the report 600 in FIG. 14 can be assembled into a QR code 700 as shown in FIG. 15 below to facilitate transmittal in a de-identified way onto a mobile application, computer, or other electronic media that has a camera 805 (FIG. 16A) to scan the QR code and automatically enter the values into a software program. The QR code can be placed at the end of the report to enable scanning the QR code directly from the printed report or that on a screen. The importance of easy transmission of the report data to another medium or software without exposing identifiers can provide displays of exam results in a useful way for referring physicians, patients, and/or other professionals.

Figure 16A:
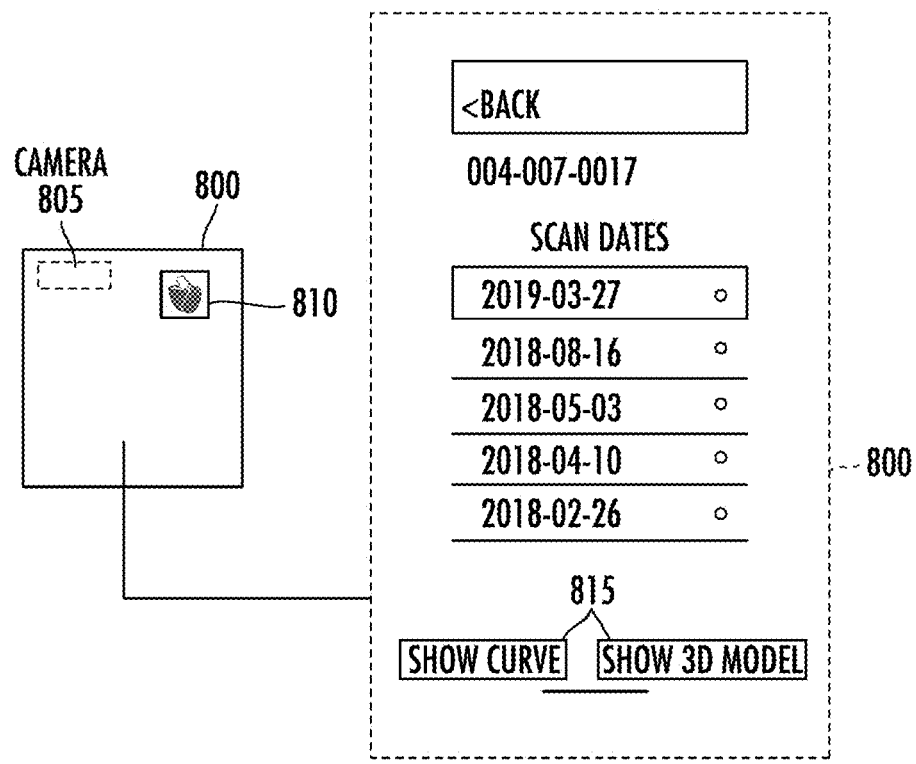
Figure 16B:
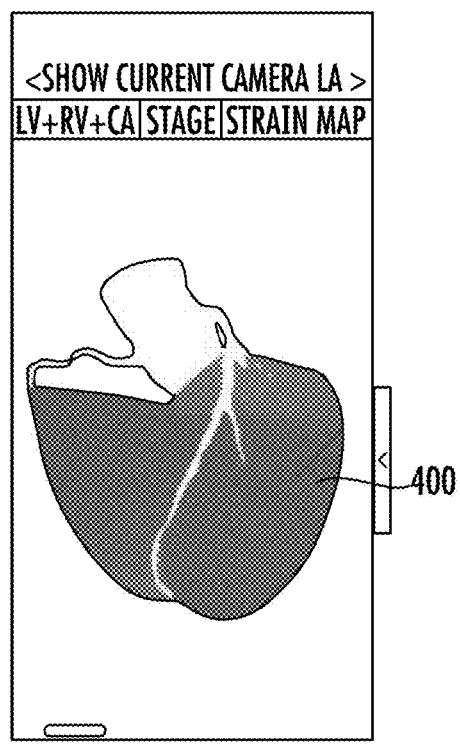

FIGS. 16A-16C show features of a mobile application embodiment that can be provided on a mobile device such as a smartphone 800 that can scan the QR code in FIG. 15 to organize the exam report data and can store the data based on patient identifiers and/or date or time point of the exam. The mobile application (also known by the acronym "APP") 810 can provide functionality for displaying the exam results and can be accessible by an icon 810i (FIG. 16A) on the mobile device 800 (or alternatively computer software or other electronic media application). The icon 810i can correspond to a shape of the 3-D model of the heart shown in FIG. 16B, for example, in one or more colors. The mobile device 800 can provide a user interface 815 that allows a user to select to display the changes in one or more risk scores $R_s$ in a graph over time (and/or other metric) as shown in FIG. 16C, and to show a 3-dimensional model 400 described previously as shown in FIG. 16B.

Beyond the Heart

Embodiments of SENC can be used to measure deformation from organs other than the heart using special timing or muscle stimulation or activation methods. Contraction of skeletal muscles can be evaluated to identify weakened areas and monitor changes in muscle strength either by peak strain, strain rates, duration of peak strain, time to peak strain, or other metrics.

Skeletal Muscle

Strain can be measured during orthopedic applications, shown for the heart previously, using devices that can cause repeated motion of target muscle and may be timed to trigger initiation of acquisition of MRI data with initiation of the induced/applied physical stimulation. In some embodiments, the rate of repetition should be at least about 30-40 times per minute. As previously described for the ECG-less acquisition, techniques that avoid the need for triggering may be utilized to adjust strain curves regardless of triggering timepoint to accurately evaluate peak strain.

Example: Imaging the muscles of the hand using a device that will send triggering signals to the MRI scanner as hand grasp and release the device about 40 times per minute, e.g., a range of 30-60 times per minute in regular or irregular successive timing during and/or between repetitions. The same technique may be used for other skeletal muscles such as the biceps, hamstring, etc.

Figure 17A:
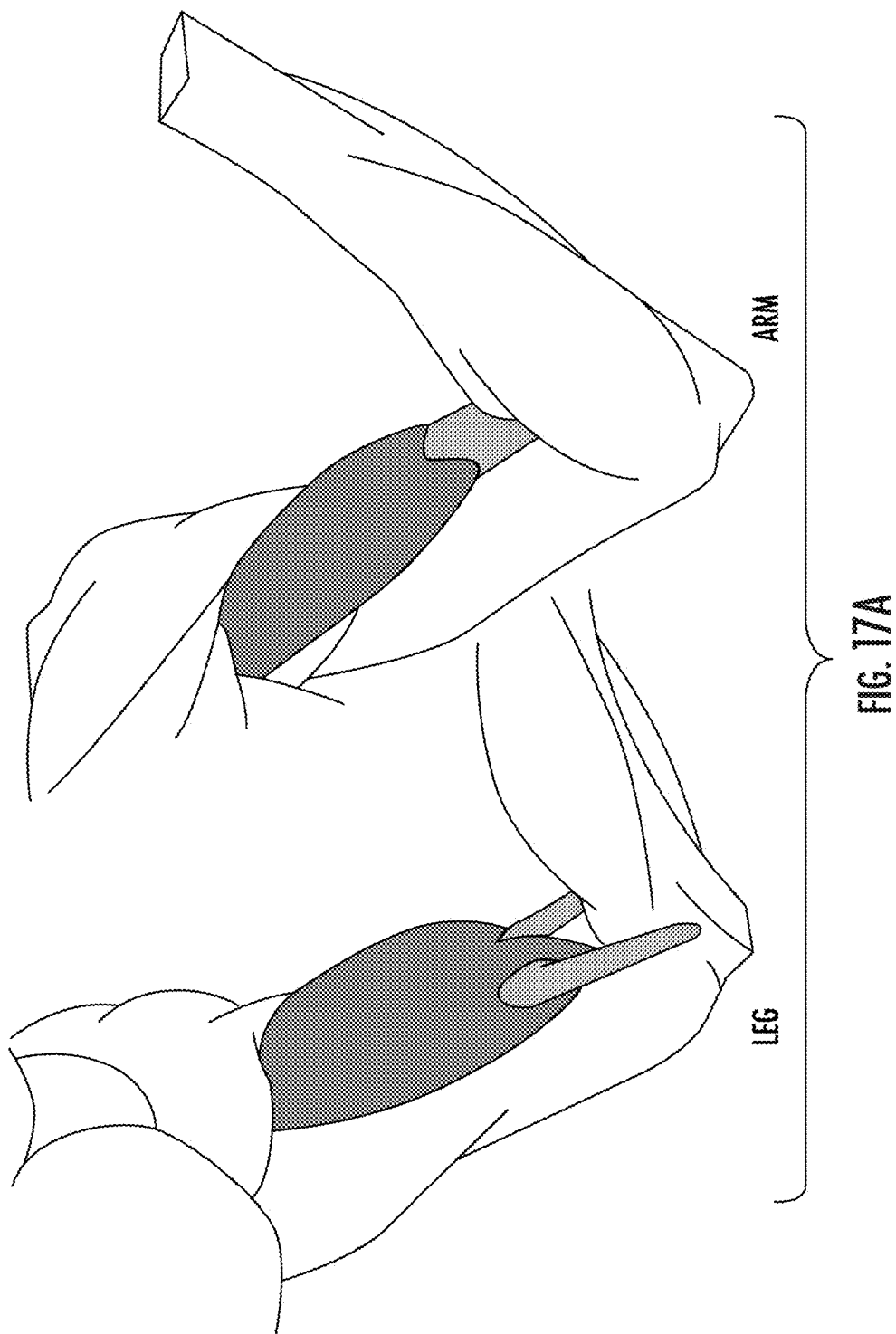
FIGS. 17A-17B are anatomical schematics of orthopedic targets that can be evaluated to measure skeletal intramuscular strain using SENC according to embodiments of the present invention.
Figures 17B, 17C:
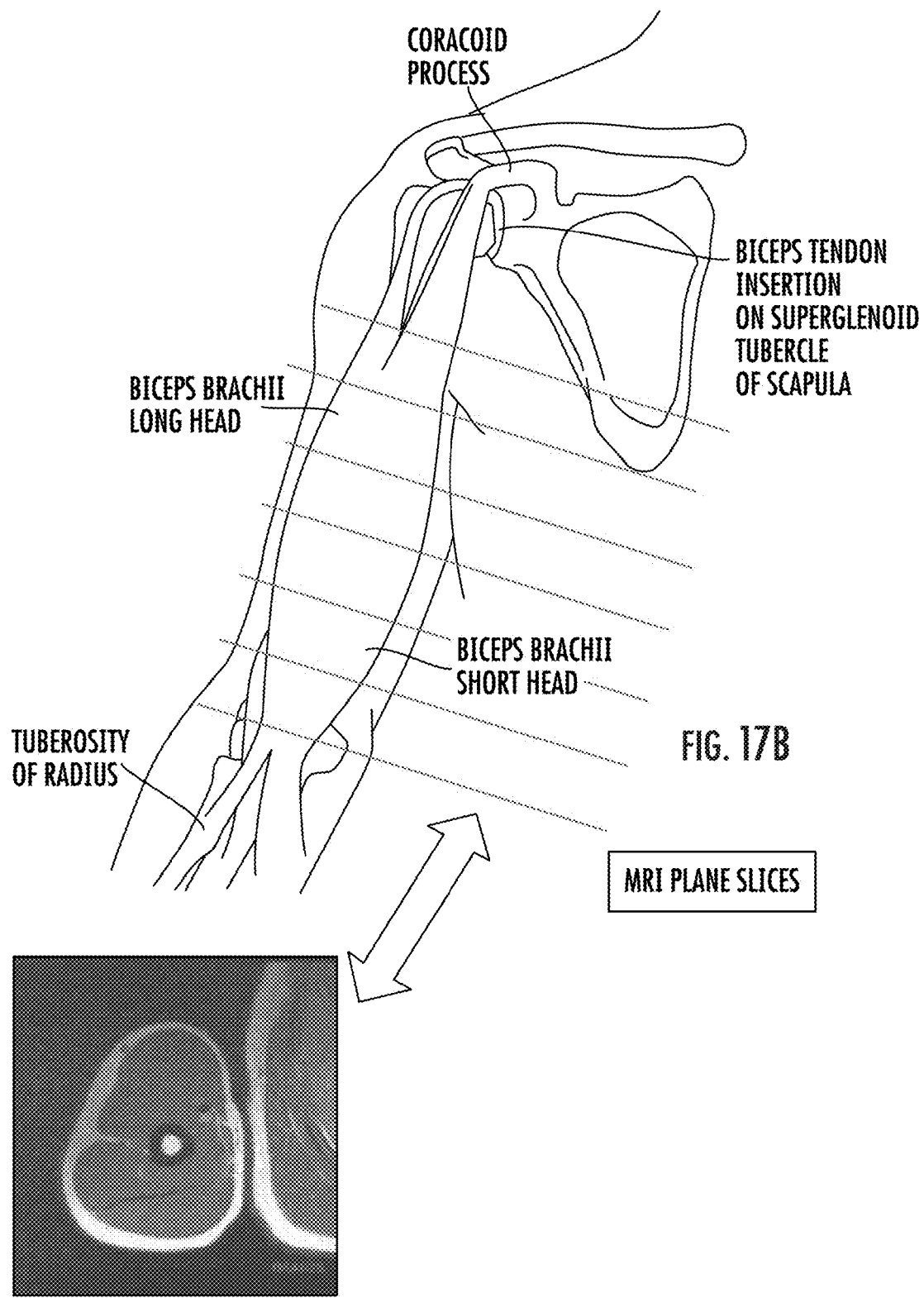
FIG. 17C is a cross-sectional view of the biceps from one of the plane orientations shown in FIG. 17B.

Using this technique of periodic activation of skeletal muscles in natural motion, we contemplate that we will be able to show muscle weakness or areas within the muscle that are dysfunctional. FIG. 17A shows examples for activating the hamstring or bicep to evaluate ability of skeletal muscles to deform during flexing. Since SENC identifies muscle deformation perpendicular to the image plane, imaging across multiple planes as shown in FIG. 17B are important to map muscle health throughout the target muscle length. FIG. 17C shows a cine image of the biceps for one of these image planes. Of course, SENC uses a different pulse sequence that creates linear tags parallel to the image plane that measures strain at a pixel-to-pixel basis perpendicular to the image plane by comparing low tuning/frequency and high tuning/frequency specified at undeformed and fully deformed muscular tissue respectively. It should be noted that alternative planes at angles relative to the muscle plane may additionally be utilized to better profile the muscle health. Both global function, regional function, and risk scores can be measured for orthopedic or other clinical applications just as performed for the heart as described above.

Figure 18:
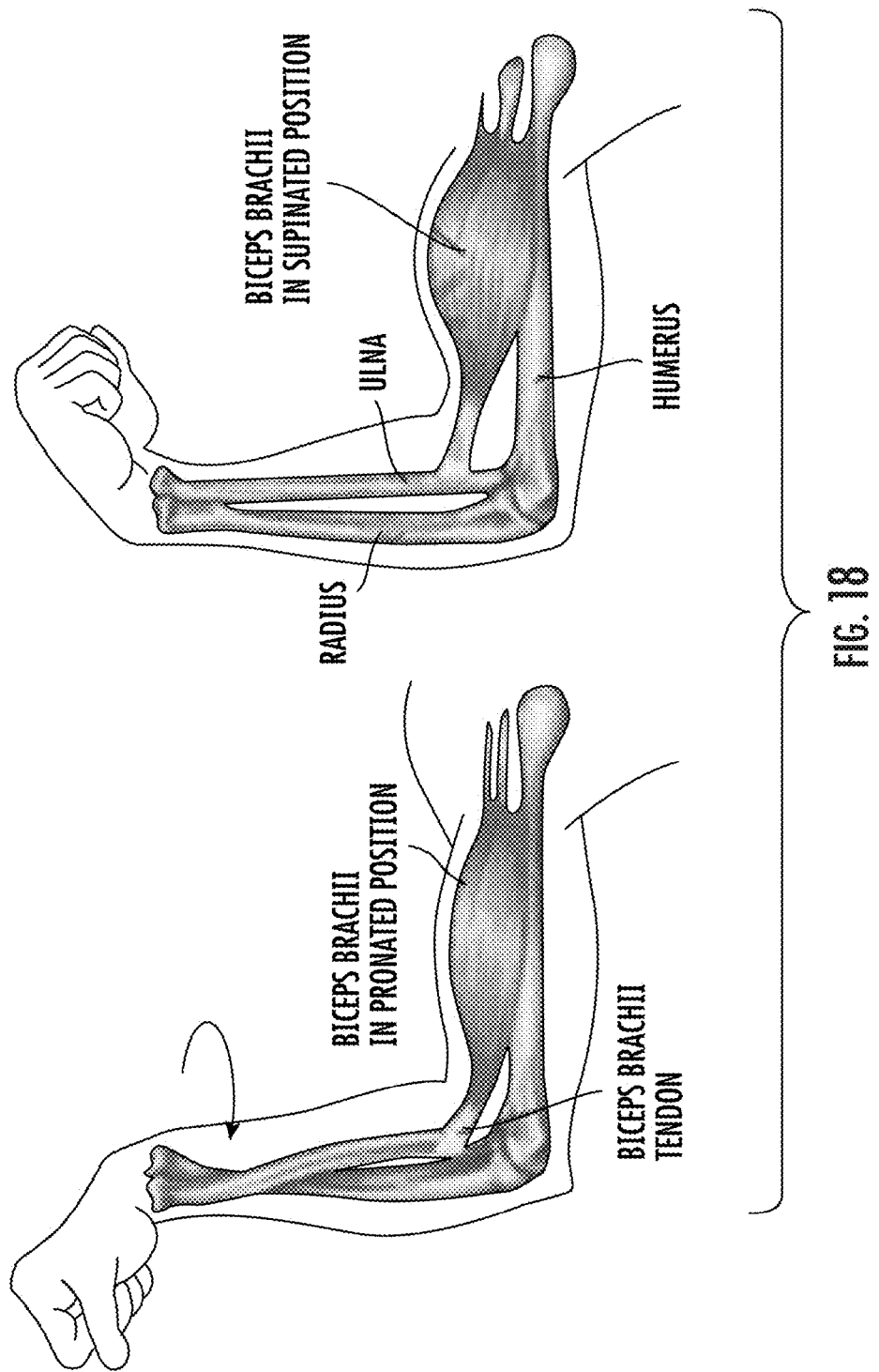
FIG. 18 illustrates anatomical schematics of ways to activate biceps to measure corresponding intramuscular strain according to embodiments of the present invention.

FIG. 18 shows a technique to measure bicep strength by activating the muscle with motion that allows maintaining the image plane during cycling of the muscle activation. This technique shows the trigger points with the arm fully extended or fully contracted. The orientation of the wrist might give different information for the diagnosis compared to purely flexing the arm or keeping the arm still while activating the muscles. Similar techniques apply to other skeletal muscles. The key for measuring strain for any muscle is to maintain the image plane throughout the cycle and provide sufficient activation to encourage deformation of the muscle fibers to compare strain at two trigger points (e.g. fully activated vs relaxed).

In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. More particularly, the workflow steps may be carried out in a different manner, in a different order and/or with other workflow steps or may omit some or replace some workflow steps with other steps. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed:

1. A method of monitoring and/or assessing cardiac health, comprising:
   directing an MRI scanner to transmit a plurality of strain encoded pulse sequences for different long and short axis views of a heart of a human patient;
   obtaining MRI images of the heart of the human patient;
   electronically calculating a plurality of strain measurements from the obtained MRI images, the plurality of strain measurements comprising a first number of defined longitudinal left ventricular segments comprising basal, mid and apical sets of strain measurements, and a second number of defined circumferential left ventricular segments comprising two-chamber, three-chamber and four-chamber long axis sets of strain measurements, wherein the first number of defined longitudinal left ventricular segments and the second number of defined circumferential left ventricular segments are added together to provide an overall number of defined left ventricular segments; and programmatically calculating a risk score, wherein the risk score is calculated based on a number of the first number of defined longitudinal left ventricular segments summed with a number of the second number of defined circumferential left ventricular segments that have a respective strain measurement value equal to or below −17% associated with peak strain of normal muscle contractibility across both genders and across different ages, divided by the overall number of the defined left ventricular segments, and wherein the risk score is provided to a patient report in a numerical range with a first end of the numerical range associated with a healthy (normal) heart and a second end of the numerical range corresponding to heart failure thereby providing a measure of current status of cardiac health.

2. The method of claim 1, wherein the obtaining and calculating steps comprise:
obtaining a plurality of parallel slices of a common (the same) single image plane to provide the obtained MRI images, each slice providing a series of images over a cardiac cycle obtained during a respective single heartbeat while the human patient is free-breathing;
and for each slice of the parallel slices,
programmatically calculating a strain value for each of a plurality of segments; and
for each segment of the plurality of segments,
programmatically combining one or more strain measurements from at least two corresponding segments of different slices of the plurality of slices to thereby generate a composite strain value for each segment, and wherein the composite strain value for each segment is the strain measurement for each corresponding segment used to calculate the risk score.

3. The method of claim 2, wherein the combining is carried out to average two or more strain values from the at least two corresponding segments of different slices.

4. The method of claim 3, wherein the average is a weighted average whereby one strain value is given a greater multiplier or weight than another for a respective segment.

5. The method of claim 2, wherein the single image plane is a two-chamber long-axis view of the heart, wherein the plurality of slices is three, and wherein the number of segments is seven.

6. The method of claim 1, wherein the obtaining and calculating steps comprise:
electronically obtaining a plurality of parallel slices of a common (the same) single image plane to provide the obtained MRI images, each slice providing a series of images over a cardiac cycle obtained during a respective single heartbeat while the human patient is free-breathing;
and for each slice of the parallel slices,
electronically calculating a strain value for each of a plurality of segments; and
for each segment of the plurality of segments,
electronically selecting a peak strain value from one of the calculated strain values of the plurality of slices as a resultant strain value for that segment, wherein the resultant strain value for that segment is the strain measurement for a corresponding segment used to calculate the risk score.

7. The method of claim 6, wherein the single image plane is a two-chamber long-axis view of the heart, wherein the plurality of slices is three, and wherein the number of segments is seven.

8. The method of claim 1, wherein the risk score defines a linear relationship of progressive left ventricular dysfunction over the numerical range.

9. The method of claim 8, wherein a mid-range value of the risk score defines an at-risk and/or pre-heart failure status.

10. The method of claim 8, wherein the numerical range is 0%-100%.

11. The method of claim 1, wherein the defined longitudinal left ventricular segments comprise: 6 basal-, 6 mid-, and 4-apical short axis, so that the first number is sixteen, wherein the defined circumferential left ventricular segments comprise: 7 two-chamber, 7 three-chamber, and 7 four-chamber long axis, so that the second number is twenty-one, and wherein the overall number of segments is at least thirty-seven.

12. The method of claim 1, wherein the calculated risk score is multiplied by 100.

13. An MRI workstation or module in communication with or configured with at least one processor and/or server configured to carry out the method of claim 1.

14. The method of claim 1, wherein the calculating the risk score is carried out to provide the calculated risk score as a value in a range of risk score values that correlates to respective stages of heart health from healthy/normal to different heart failure stages including A-D, with heart failure states A-B+ associated with an at-risk and/or pre-heart failure status of particular clinical interest for proactive management to thereby prevent clinical (typically irreversible) heart failure.

15. The method of claim 14, wherein a risk score range of possible risk scores provided by the calculated risk score for proactive management of cardiac health is from about 75% to about 50%, the method further comprising prescribing a therapy for a respective patient in response to the calculated risk score.

16. A system configured to evaluate a patient for potential interventional cardiac therapy, comprising:
an MRI workstation in communication with an MRI scanner, wherein the MRI workstation and/or a remote module in communication with the MRI workstation is configured with at least one processor and/or server configured to:
direct the MRI scanner to transmit strain encoded pulse sequences of long and short axis planes of a heart of a human patient;
obtain MRI images of the heart of the human patient;
electronically contour tissue in the obtained MRI images to delineate circumferential and longitudinal segments of the heart;
determine a plurality of strain measurements from the obtained MRI images, the plurality of strain measurements comprising respective strain measurements for a first number of defined circumferential segments and respective strain measurements for a second number of defined longitudinal segments, wherein the first number and the second number are summed to provide an overall number of segments; and
calculate a risk score based on how many of the defined longitudinal and circumferential segments have a respective strain measurement that is equal to or less than −17% associated with healthy/normal contractility at peak contraction, divided by the overall number of segments, wherein the −17% defined threshold strain measurement is a universal norm for both genders and all ages, and wherein the risk score is provided in a numerical range with a first end of the numerical range associated with a healthy (normal) heart and a second end of the numerical range corresponding to heart failure thereby providing a measure of current status of cardiac health.

17. The system of claim 16, wherein the defined longitudinal segments comprise sixteen segments: 6 basal-, 6 mid-, and 4-apical short axis, and wherein the defined circumferential segments comprise twenty one segments: 7 two-chamber, 7 three-chamber, and 7 four-chamber long axis so that the overall number of segments is at least 37 segments.

18. The system of claim 16, wherein the calculated risk score is multiplied by 100.

19. The system of claim 16, wherein the MRI workstation and/or the remote module in communication with the MRI workstation is configured with at least one processor and/or server configured to obtain the MM images of the heart and determine strain values by:

obtaining a plurality of parallel slices of a common (the same) single image plane to provide the obtained MRI images, each of the parallel slices providing a series of images over a cardiac cycle that are obtained over a respective single heartbeat while the human patient is free-breathing;

and for each slice of the parallel slices, calculating a strain value for each of a plurality of segments; and for each segment of the plurality of segments, either:

(i) combining one or more strain measurements from at least two corresponding segments of different slices of the plurality of slices to thereby generate a composite strain value for each segment, or (ii) selecting a peak strain value from one of the calculated strain values of the plurality of slices as a resultant strain value for that segment whereby either the composite strain value or the resultant strain value is used for a corresponding segment in the calculation of the risk score.

\* \* \* \* \*

UNITED STATES PATENT AND TRADEMARK OFFICE
CERTIFICATE OF CORRECTION

PATENT NO. : 11,872,019 B2
APPLICATION NO. : 16/880110
DATED : January 16, 2024
INVENTOR(S) : Nael F. Osman It is certified that error appears in the above-identified patent and that said Letters Patent is hereby corrected as shown below:

In the Specification

Column 1, Line 57: Please correct "Mill" to read --MRI--

Column 3, Line 52: Please correct "Mill" to read --MRI--

Column 9, Line 46: Please correct "MM" to read --MRI--

Column 9, Line 59: Please correct "MM" to read --MRI--

Column 12, Line 5: Please correct "Mill" to read --MRI--

Column 26, Line 19, Equation 2: Please correct "(Circumferential Segments $\leq$ -17%)" to read --(# Circumferential Segments $\leq$ -17%)--

Column 30, Lines 24-25: Please correct "$\leq$-10%" to read -->-10%--

In the Claims

Column 34, Line 64, Claim 16: Please correct "-17% defined threshold strain" to read -- -17% strain--

Column 35, Line 16, Claim 19: Please correct "MM" to read --MRI--

Signed and Sealed this
Thirtieth Day of April, 2024

Katherine Kelly Vidal
*Director of the United States Patent and Trademark Office*